(12) United States Patent  
Sakakura et al.

(10) Patent No.: US 8,598,879 B2  
(45) Date of Patent: Dec. 3, 2013

(54) MAGNETIC RESONANCE DIAGNOSTIC APPARATUS

(75) Inventors: Yoshitomo Sakakura, Nasushiobara (JP); Satoshi Sugiura, Otawara (JP); Tomoyuki Yoshida, Nasushiobara (JP); Takashi Yanashima, Otawara (JP); Masateru Iwasa, Yokohama (JP); Yutaka Kato, Utsunomiya (JP); Koji Kitamura, Yaita (JP); Kazuto Nogami, Nasushiobara (JP); Hidekazu Tanaka, Otawara (JP); Makoto Sato, Nasushiobara (JP); Shigehide Kuhara, Otawara (JP); Taketo Kawakami, Utsunomiya (JP); Yasutake Yasuhara, Nasushiobara (JP); Hiroshi Sugimoto, Utsunomiya (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 378 days.

(21) Appl. No.: 13/108,137

(22) Filed: May 16, 2011

(65) Prior Publication Data

US 2011/0279116 A1 Nov. 17, 2011

(30) Foreign Application Priority Data

May 14, 2010 (JP) .................. 2010-112454  
Mar. 31, 2011 (JP) .................. 2011-080817

(51) Int. Cl.  
*G01V 3/00* (2006.01)

(52) U.S. Cl.  
USPC ........................................ 324/318; 324/315

(58) Field of Classification Search  
USPC ............................ 324/300–322; 600/407–445  
See application file for complete search history.

(56) References Cited

U.S. PATENT DOCUMENTS 7,123,010 B2    10/2006  Kröckel  
8,309,064 B2 *  11/2012  Rosa et al. ................ 424/62

(Continued)

FOREIGN PATENT DOCUMENTS

JP     2001-231762     8/2001  
WO    91/07132 A1    5/1991  
WO    2005/110261 A2  11/2005  
WO    2008/137495 A1  11/2008

OTHER PUBLICATIONS

Office Action dated Jun. 5, 2012 in CN Application No. 201110123514.2.

(Continued)

*Primary Examiner* — Brij Shrivastav  
(74) *Attorney, Agent, or Firm* — Nixon & Vanderhye PC

(57) ABSTRACT

A magnetic resonance diagnostic apparatus is configured in such a manner that: a high-frequency transmission coil transmits a high-frequency electromagnetic wave at a magnetic resonance frequency to an examined subject; a heating coil performs a heating process by radiating a high-frequency electromagnetic wave onto the examined subject at a frequency different from the magnetic resonance frequency; based on a magnetic resonance signal, a measuring unit measures the temperature of the examined subject changing due to the high-frequency electromagnetic wave radiated by the heating coil; and a control unit exercises control so that the measuring unit measures the temperature while the heating coil is performing the heating process, by ensuring that the transmission of the high-frequency electromagnetic wave by the high-frequency transmission coil and the radiation of the high-frequency electromagnetic wave by the heating coil are performed in parallel.

20 Claims, 15 Drawing Sheets

(56) References Cited

U.S. PATENT DOCUMENTS

2007/0238976 A1    10/2007    Ishihara
2008/0269607 A1*    10/2008    Ishida et al. ................. 600/439
2009/0192383 A1    7/2009    Pananakis et al.

OTHER PUBLICATIONS

Office Action dated Mar. 4, 2013 in CN Application No. 201110123514.2.

* cited by examiner

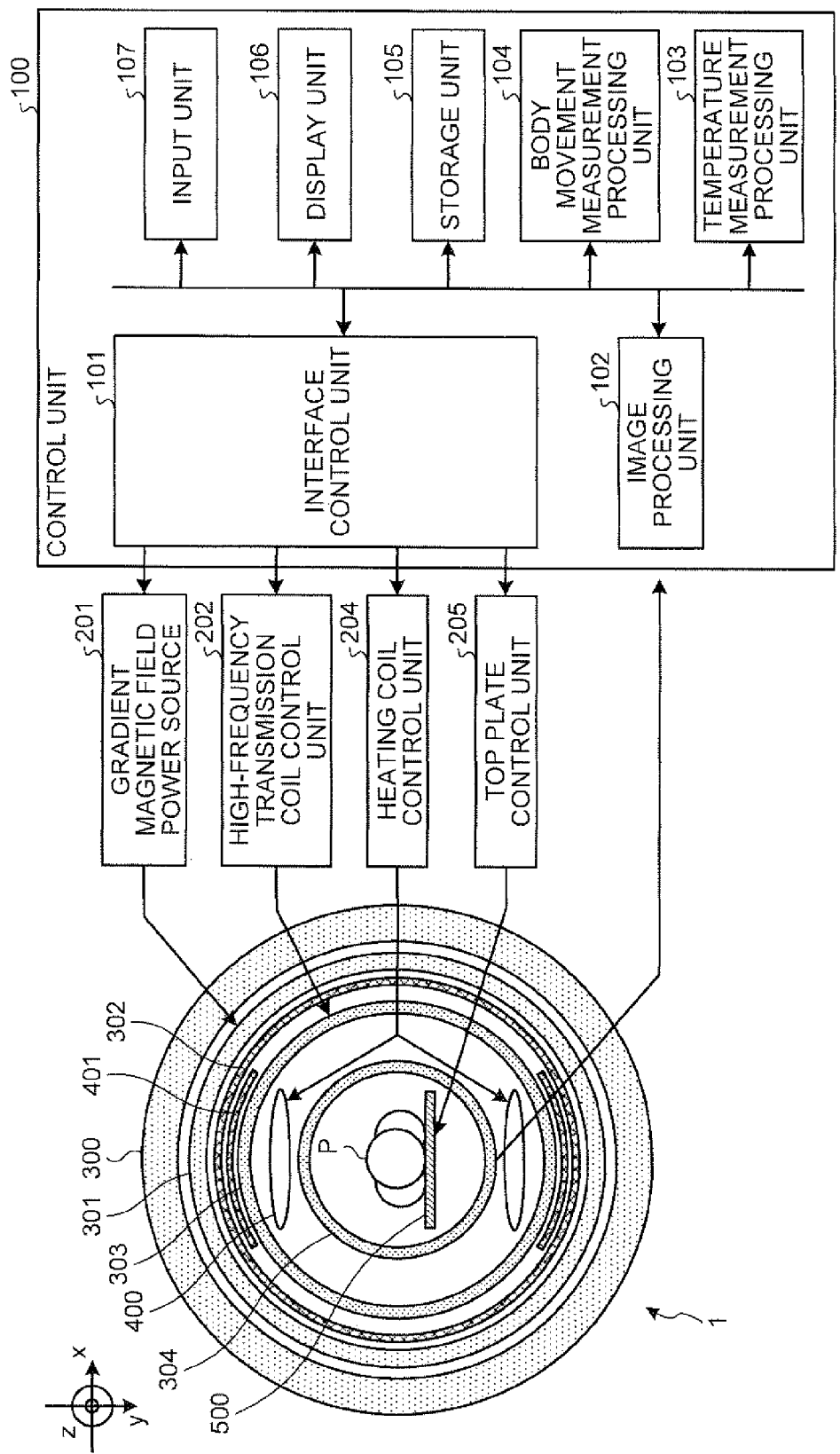

US 8,598,879 B2

MAGNETIC RESONANCE DIAGNOSTIC APPARATUS

CROSS-REFERENCE TO RELATED APPLICATIONS

This application is based upon and claims the benefit of priority from Japanese Patent Application No. 2010-112454, filed on May 14, 2010; and Japanese Patent Application No. 2011-80817, filed on Mar. 31, 2011, the entire contents of all of which are incorporated herein by reference.

FIELD

Embodiments described herein relate generally to a magnetic resonance diagnostic apparatus that collects biological information from the inside of an examined subject by utilizing magnetic resonance phenomena.

BACKGROUND

In recent years, heat treatments by which heat is applied to tumors in examined subjects so as to cause thermal necrosis have been put into practical use for the purpose of treating enlargement of the prostate gland, cancer, and the like. To perform such heat treatments more efficiently, it is necessary to understand the position of the heated region and the temperature of the heated region in each examined subject.

To understand the position and the temperature of the heated region, one of the methods that have been tried is to take a longitudinal-relaxation-period-weighted image of the body tissues of the examined subject and to measure changes in the temperature based on changes in the image, while utilizing the characteristic where the relaxation period of a magnetic resonance signal has a temperature dependency (see, for example, Japanese Patent Application Laid-open No. 2001-231762).

To perform a heat treatment by using the magnetic resonance diagnostic apparatus described above, it is necessary to provide, separately from each other, the magnetic resonance diagnostic apparatus used for measuring the changes in the temperature and the heating apparatus used for performing the heat treatment.

When the magnetic resonance diagnostic apparatus and the heating apparatus are provided in locations distant from each other, it is necessary to repeatedly perform the following steps: first, the examined subject is brought to the heating apparatus so that the heating process can be performed thereon; and subsequently, the examined subject is brought to an image taking position of the magnetic resonance diagnostic apparatus so that the temperature can be measured. In this situation, because it is not possible to perform the heating process and the temperature measuring process at the same time, it is difficult to accurately understand the changes in the temperature caused by the heating process.

Alternatively, another method is also possible by which a small-sized heating apparatus that can be inserted into the heated region of the examined subject is structured, so that a heat treatment can be performed while the examined subject is placed in the image taking position of the magnetic resonance diagnostic apparatus. This method, however, is highly invasive and causes a large burden on the examined subject because the heating apparatus needs to be inserted into the examined subject.

BRIEF DESCRIPTION OF THE DRAWINGS

FIG. 1 is a block diagram of a magnetic resonance diagnostic apparatus according to an embodiment;

DETAILED DESCRIPTION

Figure 2A:
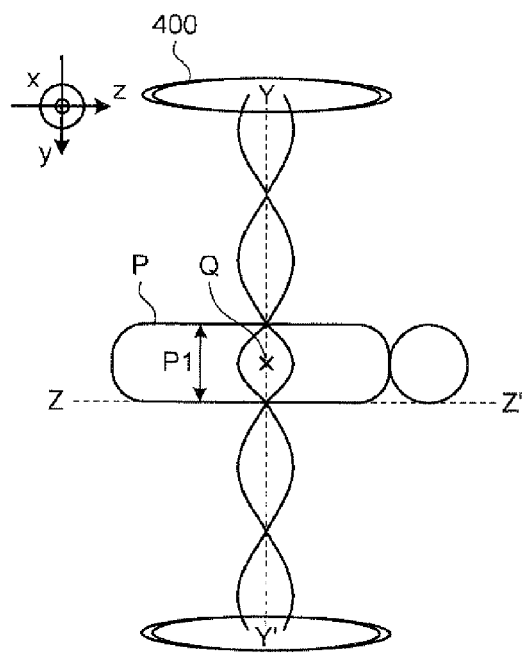
FIGS. 2A and 2B are drawings of heating coils and a heating pulse according to the embodiment.

In the following sections, exemplary embodiments will be explained with reference to the accompanying drawings.

The magnetic resonance diagnostic apparatus according to the present embodiments includes a magnetostatic field coil, a gradient coil, a high-frequency transmission coil, an image generating unit, a heating coil, a measuring unit, a control unit. The magnetostatic field coil forms a magnetostatic field. The gradient coil superimposes a gradient magnetic field onto the magnetostatic field. The high-frequency transmission coil transmits a high-frequency electromagnetic wave at a magnetic resonance frequency to an examined subject placed in the magnetostatic field. The high-frequency reception coil receives a magnetic resonance signal transmitted from the examined subject. The image generating unit generates a magnetic resonance image of the examined subject, based on the magnetic resonance signal. The heating coil performs a heating process by radiating a high-frequency electromagnetic wave onto the examined subject at a frequency different from the magnetic resonance frequency. The measuring unit, based on the magnetic resonance signal, measures a temperature of the examined subject changing due to the high-frequency electromagnetic wave radiated by the heating coil. The control unit exercises control so that the measuring unit measures the temperature while the heating coil is performing the heating process, by ensuring that the transmission of the high-frequency electromagnetic wave by the high-frequency transmission coil and the radiation of the high-frequency electromagnetic wave by the heating coil are performed in parallel.

A Configuration of a Magnetic Resonance Diagnostic Apparatus 1

FIG. 1 is a block diagram of a magnetic resonance diagnostic apparatus 1 according to an embodiment. As shown in FIG. 1, the magnetic resonance diagnostic apparatus 1 has a configuration in which the following elements are combined together: a control unit 100; a gradient magnetic field power source 201; a high-frequency transmission coil control unit 202; a heating coil control unit 204; a couchtop control unit 205; a magnetostatic field magnet 300; gradient magnetic field coils 301; a transmission coil RF shield 302; a high-frequency transmission coil 303; a high-frequency reception coil 304; heating coils 400; heating coil RF shields 401; and a couchtop 500. The configuration of the magnetic resonance diagnostic apparatus 1 is not limited to this example. It is acceptable to add or omit the constituent elements thereof, as necessary.

The magnetostatic field magnet 300, the gradient magnetic field coils 301, the transmission coil RF shield 302, the high-frequency transmission coil 303, the high-frequency reception coil 304, the heating coils 400, and the heating coil RF shields 401 are housed in a coil container that is in the form of a circular cylinder (not shown). When a heating process or an image taking process is performed on an examined subject P, the examined subject P is held in an opening of the coil container. In the following sections, the opening of the coil container will be referred to as a "patient bore".

Further, the x-axis shown in FIG. 1 is an axis corresponding to the width direction of the couchtop 500 (explained later). The y-axis shown in FIG. 1 is an axis corresponding to the direction perpendicular to the floor surface on which the magnetic resonance diagnostic apparatus 1 is placed. The z-axis shown in FIG. 1 is an axis corresponding to the length direction of the couchtop 500 or corresponding to the body axis direction of the examined subject P. The same applies to the directions of the x-axis, the y-axis, and the z-axis mentioned in the explanations of the drawings and the embodiments hereinafter.

The control unit 100 has a configuration in which a Central Processing Unit (CPU), a Read-Only Memory (ROM), a Random Access Memory (RAM), and the like are combined. Examples of function control units provided in the control unit 100 include: an interface control unit 101; an image processing unit 102; a temperature measurement processing unit 103; a body movement measurement processing unit 104; a storage unit 105; a display unit 106; and an input unit 107. The control unit 100 controls the magnetic resonance diagnostic apparatus 1 in an integral manner, by processing signals supplied from various functional units and by generating and supplying various types of control signals various functional units.

The interface control unit 101 outputs a control signal used for operating the gradient magnetic field power source 201, the high-frequency transmission coil control unit 202, the heating coil control unit 204, and the couchtop control unit 205 that are connected to the control unit 100, when an image taking process or a heating process is performed on the examined subject P. More specifically, when the image taking process is performed, the interface control unit 101 outputs a gradient magnetic field generating signal to the gradient magnetic field power source 201 and outputs an image taking RF pulse generating signal to the high-frequency transmission coil control unit 202, based an an image taking parameter being input via the input unit 107 (explained later). Further, when the heating process is performed, the interface control unit 101 outputs a heating pulse generating signal to the heating coil control unit 204, based on a heating parameter being input via the input unit 107. Furthermore, the interface control unit 101 outputs a couchtop moving signal to the couchtop control unit 205, based on a couchtop parameter being input via the input unit 107.

The image processing unit 102 generates a magnetic resonance image of the examined subject P based on a magnetic resonance signal being output from the high-frequency reception coil 304 (explained later). The image processing unit 102 generates, for example, a tomography image taken on an arbitrary cross-sectional plane of the examined subject F, as the magnetic resonance image. The image processing unit 102 generates the tomography image by, for example, mapping a transverse relaxation period collected from the magnetic resonance signal in correspondence with coordinates in the tomography image. The image processing unit 102 generates the tomography image and outputs the generated tomography image to the temperature measurement processing unit 103, the body movement measurement processing unit 104, and the storage unit 105.

The temperature measurement processing unit 103 measures a temperature distribution inside the examined subject P, based on the tomography image being output from the image processing unit 102. The temperature measurement processing unit 103 measures the temperature distribution by detecting a change in the transverse relaxation period mapped in the tomography image. This process is performed based on the fact that the transverse relaxation period of a proton spin of the body tissues of the examined subject P has a temperature dependency. The transverse relaxation period changes in proportion to changes in the temperature, in accordance with a temperature dependency coefficient, which is known in advance.

Next, the temperature measuring process performed by the temperature measurement processing unit 103 will be explained more specifically. The temperature measuring process by the temperature measurement processing unit 103 is performed by generating a temperature change image in which temperature changes of the examined subject P are mapped. At a stage prior to the temperature change image generating process, the temperature measurement processing unit 103 first sets, as a reference image, a tomography image of the examined subject P being output from the image processing unit 102 when the heating coils 400 have not yet performed the heating process (explained later). After the reference image is generated, when another tomography image of the examined subject P is output from the image processing unit 102, the temperature measurement processing unit 103 generates a subtraction image in which, for each of pixels, a difference between the reference image and the current tomography image is mapped. It means that, in each of the pixels in the subtraction image, the difference between the transverse relaxation period corresponding to the time at which the reference image was generated and the current transverse relaxation period is mapped. For each of the pixels, the temperature measurement processing unit 103 divides the difference between the transverse relaxation periods by the temperature dependency coefficient. As a result, in each of the pixels in the subtraction image, the change in the temperature of the body tissues of the examined subject P between the time at which the reference image was generated and the current time is mapped. By performing the process described here, the temperature measurement processing unit 103 generates the temperature change image.

When having generated the temperature change image, the temperature measurement processing unit 103 outputs the generated temperature change image to the display unit 106 or to the storage unit 105.

In the description of the present embodiment, the example in which the temperature change is measured by using the transverse relaxation periods is explained; however, it is also acceptable to measure the temperature change by using longitudinal relaxation periods, instead of the transverse relaxation periods. The reason is that the longitudinal relaxation periods also have a temperature dependency, like the transverse relaxation periods. Further, it is assumed that the value of each of the pixels in the tomography image that is output from the image processing unit 102 and in which the transverse relaxation periods are weighted varies depending on not only the transverse relaxation periods, but also on various other parameters such as the water density of the body tissues of the examined subject P, the longitudinal relaxation periods, a self-diffusion coefficient, and the like. To avoid errors caused by these parameters, it is also acceptable to configure the temperature measurement processing unit 103 to perform a proofreading process and/or a correcting process, as necessary.

The body movement measurement processing unit 104 measures a body movement of the examined subject P, based on the tomography images being output from the image processing unit 102. The body movement measuring process by the body movement measurement processing unit 104 is performed by extracting an outline of the examined subject P from the tomography image and detecting shifting of the outline.

Next, the body movement measuring process performed by the body movement measurement processing unit 104 will be explained more specifically. The body movement measuring process by the body movement measurement processing unit 104 is performed by generating a body movement image in which a body movement of the examined subject P is visualized. At a stage prior to the body movement image generating process, the body movement measurement processing unit 104 first extracts the outline of the examined subject P from the reference image used by the temperature measurement processing unit 103 to generate the temperature change image. To extract the outline, the body movement measurement processing unit 104 detects, for example, a position (hereinafter, simply referred to as an "edge") where the pixel value in the reference image makes a radical transition and maps a predetermined pixel value onto the coordinates corresponding to the edge. Within the tomography image output by the image processing unit 102, because the pixel values in an air region are significantly different from the pixel values in the body tissue region of the examined subject P, the boundary plane between the air and the examined subject P (i.e., the outline of the examined subject P) appears in the image (hereinafter, simply referred to as an "edge image") obtained by mapping the edge. After the edge image of the reference image is generated, when another tomography image of the examined subject P is output from the image processing unit 102, the body movement measurement processing unit 104 generates an edge image with respect to the output tomography image and further generates a subtraction image in which, for each of pixels, a difference between the latter edge image and the edge image of the reference image is mapped, as the body movement image. In the body movement image, a difference between the outline of the examined subject P obtained when the reference image was generated and the current outline of the examined subject P is mapped. If the examined subject P has had a body movement since the time at which the reference image was generated, double outlines appear. On the contrary, if the examined subject P has had no body movement, the value of each of the pixels is canceled out by the difference, and nothing appears in the image. In other words, it is possible to measure the degree of the body movement of the examined subject P, based on the body movement image. The body movement measurement processing unit 104 outputs the generated body movement image to the display unit 106 or to the storage unit 105.

In the description of the present embodiment, the example is explained in which the body movement of the examined subject P is detected based on the edge image obtained by detecting the outline of the examined subject P; however, the configuration of the magnetic resonance diagnostic apparatus 1 is not limited to this example. It is also acceptable to measure the body movement of the examined subject P based on various other images such as an image in which an edge area is filled in, instead of the edge image. When a difference between two images in which the edge area is filled in is obtained, a generated subtraction image indicates an area resulting from the movements of the examined subject P as a filled-in area. By detecting the size of the filled-in area, a user of the magnetic resonance diagnostic apparatus 1 is able to visually recognize the degree of the movements of the examined subject P. Further, although the description above indicates that the body movement measurement processing unit 104 measures the body movement by generating the body movement image, another arrangement is acceptable in which, instead of generating the body movement image, the body movement measurement processing unit 104 calculates a distance between the respective outlines in the two edge images and outputs the calculated distance as an index value indicating the degree of the body movement to the display unit 106 or to the storage unit 105. The reason can be explained as follows: The larger the body movement of the examined subject P is, the larger is the shifting of the outline, and therefore, the larger is the distance between the two outlines. In other words, the larger the body movement is, the larger is the calculated index value.

The storage unit 105 has a configuration in which storage media such as a ROM, a RAM, a Hard Disc Drive (HDD), and the like are combined. The storage unit 105 stores therein the tomography images being output from the image processing unit 102, the temperature change image being output from the temperature measurement processing unit 103, the body movement image being output from the body movement measurement processing unit 104, and the like. Further, the storage unit 105 also stores therein coordinate information that is input via the input unit 107 (explained later) and that specifies a region (hereinafter, simply referred to as a "treatment region R") of the examined subject P to which a heat treatment should be applied.

The display unit 106 is configured with, for example, a liquid crystal display device or the like and displays the tomography images being output from the image processing unit 102, the temperature change image being output from the temperature measurement processing unit 103, the body movement image being output from the body movement measurement processing unit 104, and the like. Further, the display unit 106 also displays an operation screen used for operating the magnetic resonance diagnostic apparatus 1 as well as the image taking parameter, the heating parameter, the couchtop parameter, the treatment region R, and the like that are input via the input unit 107 (explained later) and are used by the magnetic resonance diagnostic apparatus 1.

The input unit 107 is configured with, for example, a touch panel display, a mechanical button, and the like and receives an input resulting from an operation performed thereon by the user. According to the received input, the input unit 107 outputs the input of the image taking parameter, the heating parameter, the couchtop parameter, or the treatment region R, or an image taking process starting/stopping instruction, a heating process starting/stopping instruction, or the like, to the interface control unit 101.

The magnetostatic field magnet 300 is used as a superconductive coil or a normal conductive coil and generates a uniform magnetostatic field in the patient bore. For example, the magnetostatic field magnet 300 generates a magnetostatic field of which the magnetic field direction is oriented in the z-axis direction shown in FIG. 1. When the magnetostatic field magnet 300 is used as a superconductive coil, a cooling mechanism (not shown) used for cooling the magnetostatic field magnet 300 is attached thereto. The cooling mechanism keeps the magnetostatic field magnet 300 in a superconductive state by cooling the magnetostatic field magnet 300. To enhance uniformity of the magnetostatic field, it is also acceptable to provide a shim coil, an iron shim, or the like, in the surrounding of the magnetostatic field magnet 300.

The gradient magnetic field coils 301 are coils that are provided on the inside of the magnetostatic field magnet 300 and that generate a gradient magnetic field within the patient bore by receiving an electric signal being output from the gradient magnetic field power source 201. Three pairs of gradient magnetic field coils 301 are provided on the inside of the magnetostatic field magnet 300, in correspondence with the x-, the y-, and the z-axes that are shown in FIG. 1, respectively. The three pairs of coils each receive the electric signal being output from the gradient magnetic field power source 201 and each generate a magnetic field that is along a different one of the x-, the y-, and the z-axes. The gradient magnetic field power source 201 forms a gradient magnetic field along an arbitrary direction by causing the three pairs of coils to generate the magnetic fields and combining the magnetic fields each of which is along a different one of the axes.

The high-frequency transmission coil 303 is a coil that is provided on the inside of the gradient magnetic field coils 301 and that receives an electric signal being output from the high-frequency transmission coil control unit 202 and transmits a Radio Frequency (RE) wave to the examined subject P. To cause a nuclear magnetic resonance in the body tissues of the examined subject P with the use of the RE wave, the high-frequency transmission coil control unit 202 applies the electric signal, while controlling the frequency so that the frequency of the RF wave corresponds to the Larmor frequency. The frequency of the RE wave changes according to the size of magnetostatic field formed by the magnetostatic field magnet 300. For example, when the size of the magnetostatic field is 3 T, 128 megahertz is used as the frequency of the RE wave. As another example, when the size of the magnetostatic field is 1.5 T, 64 megahertz is used as the frequency of the RF wave.

The high-frequency reception coil 304 is a coil provided in a position that is inside the high-frequency transmission coil 303 and the heating coils 400 (explained later) and is near the examined subject P. The high-frequency reception coil 304 receives a magnetic resonance signal transmitted from the examined subject P in correspondence with the RE wave transmitted from the high-frequency transmission coil 303. The high-frequency reception coil 304 outputs the received magnetic resonance signal to the image processing unit 102.

The heating coils 400 are ring-shaped coils provided between the high-frequency transmission coil 303 and the high-frequency reception coil 304. For example, one pair of heating coils 400 is provided so as to oppose each other and so as to have the examined subject P interposed therebetween. Each of the heating coils 400 has a small radius, so as to be able to apply a heating pulse (explained later) to a heated region Q within the examined subject P, in a concentrated manner. More specifically, the radius of each of the heating coils 400 is smaller than the radius of the high-frequency transmission coil 303 (or the coil container) and than the length of the examined subject P in the body axis direction. For example, each of the heating coils 400 is configured so as to have a radius of 10 centimeters to 30 centimeters approximately. In the description of the present embodiment, the example in which each of the heating coils 400 is configured in the form of a single ring is explained; however, each of the heating coils 400 may be configured with a coil wound like a spring or may be configured with rings that are piled on top of one another. The radius of each of the heating coils 400 may have an arbitrary length, instead of the length described in the present embodiment. The heating coils 400 receive an electric signal being output from the heating coil control unit 204, and at least one of the pair radiates an electromagnetic wave onto the examined subject P at a frequency based on information in the electric signal. The electromagnetic wave applied to the examined subject P causes a dielectric heating phenomenon in the body tissues of the examined subject P, so as to raise the temperature of the body tissues. The heating process performed on the body tissues by using the heating coils 400 will be explained in detail later.

The couchtop 500 is a plate-like member on which the examined subject P can be placed lying down. A motor (not shown) is attached to the couchtop 500. The position of the couchtop 500 can be moved along the x-, the y-, and the z-axes, in accordance with an electric signal being output from the couchtop control unit 205.

The heating process performed on the examined subject P

In the following sections, the heating process performed on the examined subject P by using the heating coils 400 will be explained. As explained above, at least one of the pair of heating coils 400 radiates the high-frequency electromagnetic wave (hereinafter, simply referred to as a "heating pulse") onto the examined subject P. The frequency of the heating pulse can be arbitrarily selected from various frequencies ranging from a number of megahertz to thousands of megahertz. It should be noted, however, that the resonant frequency of the RF wave transmitted by the high-frequency transmission coil 303 should be excluded from the choices for the frequency of the heating pulse. The frequency band to be excluded in relation to the resonant frequency corresponds to the frequencies at which the body tissues of the examined subject P cause proton spins and transmit magnetic resonance signals. The excluded frequency band may be, for example, a frequency band from 127 megahertz to 129 megahertz, when the size of the magnetostatic field is 3 T. If the frequency of the heating pulse was within the frequency band that should be excluded, the body tissues of the examined subject P would generate magnetic resonance signals due to the electromagnetic wave, so that the magnetic resonance signals would show up as an artifact in the tomography images generated by the image processing unit 102.

Next, the heating process on the examined subject P realized by the heating pulse will be explained. The heating pulse reaches the body tissues of the examined subject P. When a focus is placed on the heating pulse at a point in time, an electric field component included in the heating pulse, which is the electromagnetic wave, causes a polarization in the body tissues of the examined subject P. By the polarization, polar dipoles each made of a combination of one or more electrons, protons, and ions in the body tissues are rotated so that the direction of the polarization matches the direction of the electric field. Because the heating pulse periodically oscillates based on the frequency thereof, when a focus is placed on the heating pulse at another point in time that is a little later than the abovementioned point in time, the direction of the electric field is different from the one observed at the abovementioned point in time. The polar dipoles of the examined subject P also rotate in accordance with the change in the direction of the electric field, so that the direction of the polarization matches the direction of the electric field.

When the changes of the polar dipoles are observed over the course of time, the polar dipoles rotate in synchronization with the heating pulse, which changes the direction of the electric field based on the frequency. In this situation, when the frequency of the heating pulse is a high frequency exceeding a number of megahertz, the polar dipoles also rotate at a high speed so as to match the direction of the electric field that changes at a high speed. Such radical movements of the polar dipoles cause frictions between the polar dipoles, and the frictions generate heat in the body tissues. As a result of the phenomenon described here, the body tissues onto which the heating pulse is radiated are heated.

The heating pulse radiated from one of the pair of heating coils 400 first propagates through the air and enters into the body tissues of the examined subject P, before exiting into the air again and entering into the other of the pair of heating coils 400 provided at the other end. When a focus is placed on the boundary plane between the air and the body tissues, a boundary condition is satisfied between the electromagnetic wave that propagates through the air and the electromagnetic wave that propagates through the body tissues. In other words, when a focus is placed on the electromagnetic wave that enters into the examined subject P after going through the air, the electric field strength obtained by adding together the electric field that enters into the body tissues of the examined subject P from the air at the boundary plane, the electric field that is reflected at the boundary of the examined subject P so as to exit into the air, and the electric field that exits into the air from the body tissues of the examined subject P is equal to zero. As a result, it is possible to assume that the electromagnetic wave propagates while using the boundary plane between the air and the examined subject P as a fixed end. The same applies to the electromagnetic wave that propagates through the examined subject P and exits into the air.

Figure 2B:
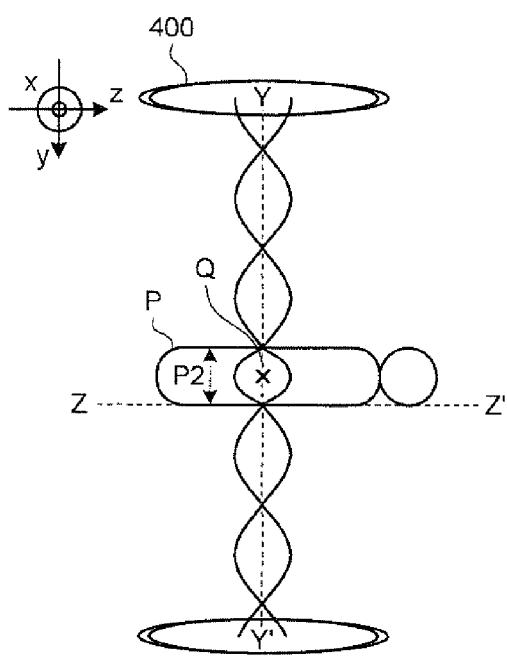

Next, let us discuss an axis Y-Y' that connects together the centers of the pair of heating coils 400. (It is assumed hereinafter that the axis Y-Y' extends parallel to the y-axis shown in FIG. 1). A part of the electromagnetic wave radiated from the heating coil 400 propagates along the axis Y-Y'. When the thickness of the examined subject P along the axis Y-Y' (i.e., the distance on the y-axis) is expressed as P1, if a condition is satisfied where an integral multiple of a half wavelength of the electromagnetic wave within the examined subject P is equal to P1, a standing wave oscillates within the examined subject P. In FIGS. 2A and 2B, the manner in which the electromagnetic wave radiated from the heating coil 400 oscillates as a standing wave is shown. In FIG. 2A, the manner in which a heating pulse having a wavelength "2×P1" within the examined subject P is radiated from the heating coil 400 is shown, while the thickness of the examined subject P on the axis Y-Y's is expressed as P1. As explained above, because the boundary plane between the body tissues of the examined subject P and the air functions as a fixed end, the electromagnetic wave that propagates through the body tissues oscillates as a standing wave in the fundamental mode of which the node corresponds to the boundary plane and of which the anti-node corresponds to the middle point of the examined subject P on the Y-Y' axis.

When a focus is placed on an electric field amplitude of the electromagnetic wave that causes the standing wave to oscillate within the examined subject P on the Y-Y' axis, the electric field amplitude is at a maximum at the middle point of the examined subject P, which corresponds to the anti-node of the standing wave. Thus, the heat applied to the body tissues is at a maximum at the middle point of the examined subject P. In the present embodiment, the heating coil control unit 204 applies the heat to the middle point, which corresponds to the anti-node of the standing wave, by controlling the electromagnetic wave in such a manner that the electromagnetic wave oscillates in the fundamental mode within the examined subject P. During such a heat treatment, it is important to ensure that the applied heat is concentrated in a tumor portion, which is the treatment region R, so as to minimize the impact of the applied heat on other normal tissues. According to the present embodiment, it is possible to efficiently perform the heating process in a specific portion because the energy of the electromagnetic wave propagating through the examined body P is arranged to be concentrated at the middle point (hereinafter, a region at which the energy of the electromagnetic wave is concentrated and on which the heating process is performed will be simply referred to as a "heated region Q").

In the example described above, the situation in which the thickness of the examined subject P is equal to P1, whereas the wavelength of the heating pulse is equal to 2×P1 is explained; however, the thickness of the examined subject P varies depending on the physique and the gender of each examined subject. To cause the standing wave to oscillate within the examined subject P, the heating coil control unit 204 needs to change the wavelength of the heating pulse depending on the thickness of the examined subject P that varies. In FIG. 2B, a heating process being performed when the thickness of the examined subject P is equal to P2, which is smaller than P1, is shown. To accommodate the examined subject P whose thickness is equal to 2P, the heating coil control unit 204 radiates a heating pulse, after changing the frequency thereof in such a manner that the wavelength is equal to 2×P2 within the body tissues. With this arrangement, it is possible to cause the electromagnetic wave to oscillate in the fundamental mode on the Y-Y' axis of the examined subject P. A method for measuring the thickness of the examined subject P will be explained in detail later.

Position Control of the Heated Region Q

In the oscillation of the standing wave described above, because the fundamental-mode standing wave is oscillated so that the node thereof corresponds to the boundary between the examined subject P and the air, the heated region Q is positioned at the middle point of the examined subject P. In that situation, when the treatment region R is at the middle point of the examined subject P, it is possible to perform the heat treatment; however, when the treatment region R is, for example, positioned near the surface of the examined subject P, the heated region Q does not coincide with the treatment region R. To make the heated region Q coincide with the treatment region R, according to the present embodiment, the heating pulse is radiated while a pad 600 used for adjusting the substantive thickness of the examined subject P is placed on the examined subject P.

Figure 3A:
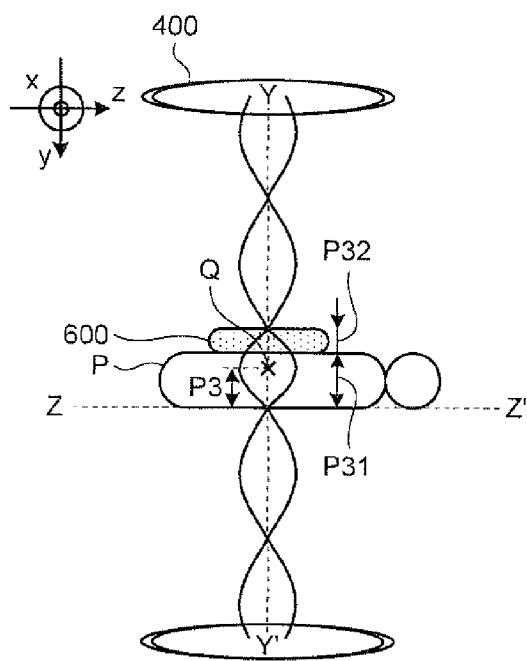
FIGS. 3A and 3B are drawings for explaining a manner in which the position of a heated region is adjusted by using a pad, according to the embodiment.
Figure 3B:
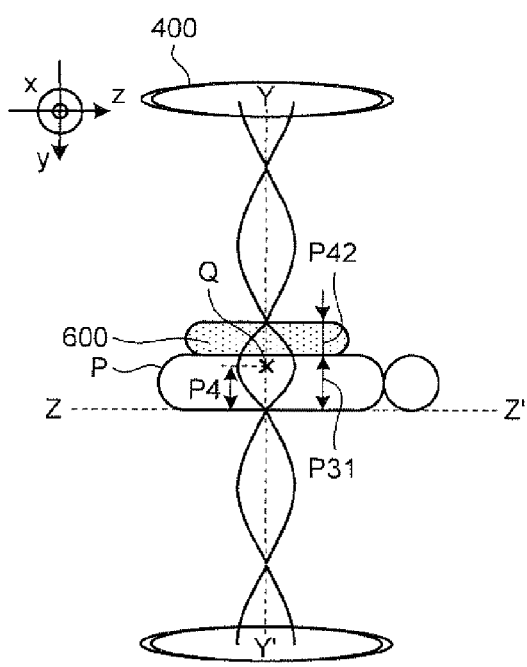

The pad 600 is a constituent element filled with a medium having an electric permittivity close to that of the body tissues of the examined subject P. The medium may be, for example, baby oil or rice. Because the electric permittivity of the medium in the pad 600 is sufficiently close to the electric permittivity of the body tissues, when a focus is placed on the electromagnetic wave entering into the examined subject P from the pad 600, no reflection of the electromagnetic wave occurs on the boundary plane between the pad 600 and the examined subject P so that the electromagnetic wave propagates from the pad 600 to the examined subject P, while the influence of the boundary plane is negligible. FIGS. 3A and 3B are drawings of heating processes being performed while the pad 600 is placed on the examined subject P. In FIG. 3A, an example is shown in which a heating process is performed on the body tissues that are positioned on the Y-Y' axis of the examined subject P, at a distance of P3 from a bottom plane (i.e., a plane corresponding to the Z-Z' axis shown in FIG. 3A) of the examined subject P on the y-axis. In the explanation below, a distance from the bottom plane of the examined subject P on the y-axis will be simply referred to as a "height". To perform the heating process on the body tissues positioned at the height P3, the pad 600 having such a thickness that makes the distance P3 correspond to the middle point should be placed on the examined subject P. In other words, when the thickness of the examined subject P is expressed as P31, the user places to place the pad 600 having a thickness P32 on the examined subject P, where a condition P3=P31±P32 is satisfied. Accordingly, the substantive thickness of the examined subject P with respect to the heating pulse can be expressed as follows: P31+P32=2×P3. Thus, the heating coil control unit 204 radiates a heating pulse after changing the frequency thereof in such a manner that the frequency is equal to 2×P3 within the body tissues. As a result, along the Y-Y' axis, a fundamental-mode standing wave oscillates at the bottom plane of the examined subject P (i.e., the point at which the y coordinate value is the largest in FIG. 3A) and at an upper plane of the pad 600 (i.e., the point at which the y-coordinate value is the smallest in FIG. 3A). Because the anti-node of the fundamental-mode standing wave is at the height P3, it is possible to perform the heating process while the treatment region R coincides with the heated region Q.

In contrast, in FIG. 3B, an example is shown in which a heating process is performed on the body tissues that are positioned at a height P4 of the examined subject P whose thickness is equal to P3, which is the same as in the example shown in FIG. 3A. To perform the heating process on the body tissues positioned at the height. P4, the pad 600 having a thickness that makes the distance P4 correspond to the middle point should be placed on the examined subject P. In other words, when the thickness of the examined subject P is expressed as P31, the user places the pad 600 having a thickness P42 on the examined subject P, where a condition P4=P31+P42 is satisfied. Thus, the heating coil control unit 204 radiates a heating pulse after changing the frequency thereof in such a manner that the frequency is equal to 2×P4 within the body tissues.

As explained above, the user selects the pad 600 having an appropriate thickness and places the selected pad 600 on the examined subject P, in accordance with the height of the treatment region R of the examined subject P. The heating coil control unit 204 causes the heating pulse to be radiated after changing the frequency thereof in accordance with a sum of the thickness of the examined subject P and the thickness of the pad 600. By performing such an operation, it is possible to arbitrary change the height of the heated region Q.

In the description of the present embodiment, the example is explained in which the treatment region R is positioned on the upper surface side of the examined subject P (i.e., the treatment region R is in a position higher than P31/2 in FIGS. 3A and 3B); however, the present embodiment is applicable even if the treatment region R is positioned on the lower surface side of the examined subject P (i.e., the treatment region R is in a position lower than P31/2 in FIGS. 3A and 3B). In that situation, for example, the examined subject P can be turned from a supine position to a prone position, so that the pad 600 is placed on top of the examined subject P after the examined subject P is turned and so that the heating process can be performed on the treatment region R after the examined subject P is turned.

Next, an operation to control the position of a heated region with respect to the x-axis direction and the z-axis direction shown in FIG. 1 will be explained.

Figure 4A:
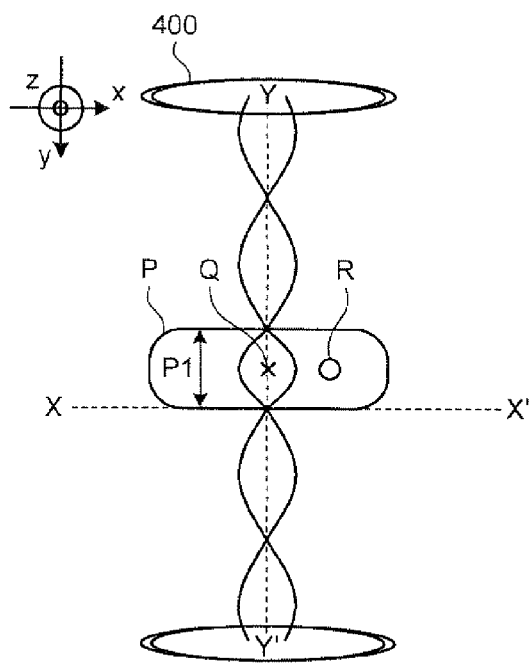
FIGS. 4A and 4B are drawings for explaining a manner in which the position of a heated region is adjusted by moving a couchtop, according to the embodiment.

In FIG. 4A, a manner in which a heating process is performed while the position of the heated region Q does not coincide with the position of the treatment region R on the x-axis is shown. As explained above, the heating pulse causes a standing wave to oscillate along the Y-Y' axis connecting the centers of the heating coils 400 together, so that the heat is applied to the heated region Q corresponding to the middle point on the Y-Y' axis. Accordingly, if the position of the heated region Q does not coincide with the position of the treatment region R on the x-axis or on the z-axis, it is not possible to apply the heat to the treatment region R efficiently.

Figure 4B:
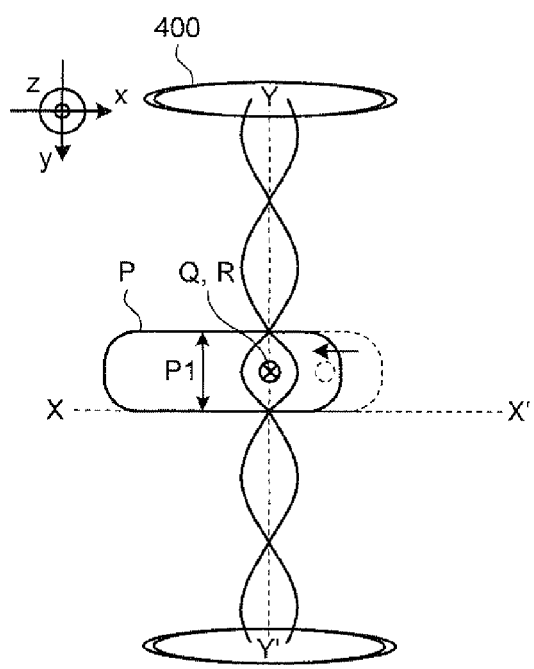

In this situation, to make the heated region Q coincide with the treatment region R, according to the present embodiment, a relative positional relationship between the examined subject P and the heating coils 400 is changed by moving the couchtop 500 under the control of the couchtop control unit 205. More specifically, the couchtop 500 is moved on an x-z plane in such a manner that the coordinates of the heated region Q on the x-z plane coincide with the coordinates of the treatment region R on the x-z plane, i.e., in such a manner that the coordinates of the Y-Y' axis on the x-z plane coincide with the coordinates of the treatment region R on the x-z plane, as shown in FIG. 4B.

When a heating pulse is radiated while the coordinates of the Y-Y' axis on the x-z plane coincide with the coordinates of the treatment region R on the x-z plane, the position at which the standing wave oscillates coincides with the treatment region R. Because the oscillating position of the standing wave coincides with the treatment region R, the heated region Q where the electric fields are concentrated coincides with the treatment region R, and it is therefore possible to apply the heat to the treatment region R in a concentrated manner.

By performing the process described above, the magnetic resonance diagnostic apparatus 1 according to the present embodiment performs the heat treatment while the spatial position of the heated region Q is arranged to coincide with the spatial position of the treatment region R.

A Flow of the Heat Treatment

Next, a flow of the heat treatment will be explained.

First, at a stage prior to the heating process, the control unit 100 sets a treatment region R and performs a pre-processing process so as to cause the heated region Q to coincide with the treatment region R. More specifically, the control unit 100 first takes a tomography image of the examined subject P. In other words, the interface control unit 101 outputs control signals to the gradient magnetic field power source 201 and to the high-frequency transmission coil control unit 202. Further, the gradient magnetic field power source 201 operates so that the gradient magnetic field coils 301 apply a gradient magnetic field to the examined subject P. Also, the high-frequency transmission coil control unit 202 exercises control so that the high-frequency transmission coil 303 transmits an RE wave to the examined subject P. When the high-frequency reception coil 304 has received the magnetic resonance signal transmitted from the examined subject P, the image processing unit 102 receives the magnetic resonance signal. Based on the received magnetic resonance signal, the image processing unit 102 generates a tomography image taken on an arbitrary cross-sectional plane of the examined subject P and outputs the generated tomography image to the display unit 106.

By visually observing the tomography image being output from the image processing unit 102, the user checks the shape of the examined subject P and the position of an affected site on which a heat treatment is to be performed. If the affected site does not appear in the tomography image displayed on the display unit 106, and if the user is not able to recognize the position of the affected site, the user operates the input unit 107 and outputs a control signal to the image processing unit 102, so as to change the tomography image generating position. In response to the received control signal, the image processing unit 102 changes the tomography image generating position, generates another tomography image of the examined subject P with respect to a cross-sectional plane specified by the control signal, and outputs the newly-generated tomography image to the display unit 106. The operation to change the tomography image generating position is repeatedly performed until the user becomes able to recognize the position of the affected site in the tomography image.

Figure 5A:
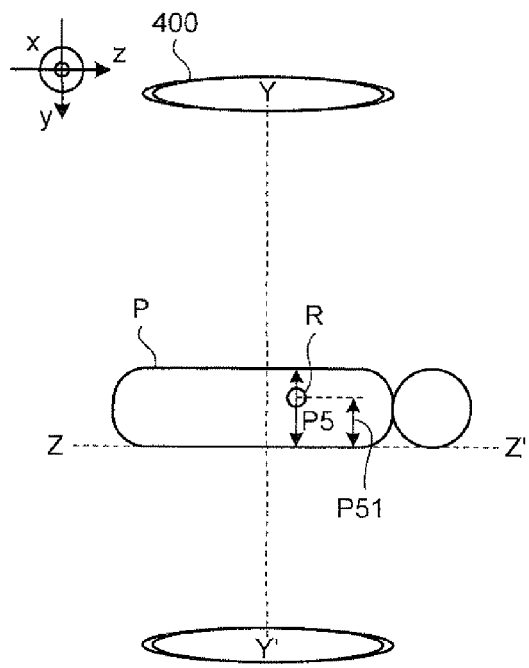
FIGS. 5A and 5B are drawings of an operation to cause a heated region and a treatment region to coincide with each other, according to the embodiment.
Figure 5B:
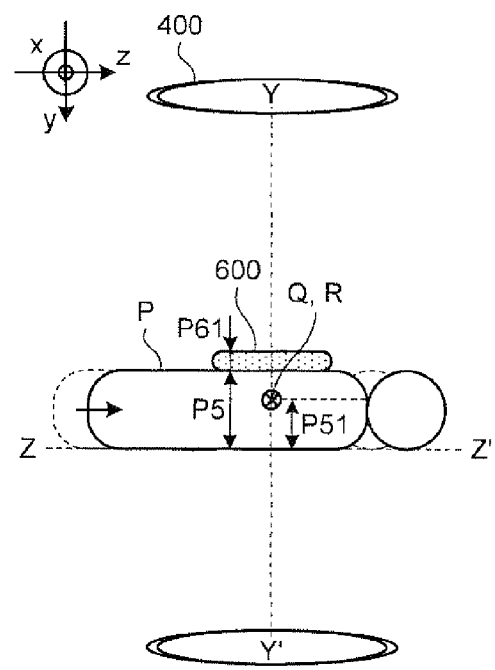

In FIG. 5A, an example of a tomography image of the examined subject P is shown. In FIGS. 5A and 5B, to simplify the explanation, the heating coils 400 are depicted in the drawings. When the user recognizes the position of the affected site in the tomography image displayed on the display unit 106, the user operates the input unit 107 so as to specify the position of the affected site as a treatment region R. In the tomography image displayed on the display unit 106, the treatment region R is specified as a circular area that encloses the affected site therein. The present embodiment is not limited to this example. For example, the treatment region R may be specified as a rectangular-shaped area. Alternatively, the treatment region R may be specified as a spherical three-dimensional region having depth information for the depth direction (i.e., the x-axis direction shown in FIGS. 5A and 5B).

When the treatment region R is specified, the control unit 100 obtains coordinates information of the treatment region R on the x-z plane. When the control unit 100 obtains the coordinate information of the treatment region R on the x-z plane, the control unit 100 compares the obtained coordinate information with coordinate information of the Y-Y' axis on the x-z plane that is stored in the storage unit 105 in advance. Based on the comparison between the coordinate information of the treatment region R on the x-z plane with the coordinate information of the Y-Y' axis on the x-z plane, the control unit 100 calculates a moving direction and a moving distance that are required to cause the treatment region R to coincide with the Y-Y' axis on the x-z plane. The interface control unit 101 outputs the moving direction and the moving distance on the x-z plane that are calculated, to the couchtop control unit 205. The couchtop control unit 205 moves the couchtop 500 as well as the examined subject P placed on the couchtop 500, in such a manner that the treatment region R coincides with the Y-Y' axis on the x-z plane. As a result of the operation described above, the examined subject P is moved an the x-z plane, so that the coordinates of the treatment region R on the x-z plane coincide with the coordinates of the Y-Y' axis on the x-z plane.

Further, when the treatment region R is specified, the control unit 100 measures the thickness of the examined subject P in a location where the treatment region R is present. More specifically, the control unit 100 measures the length of a straight line that, in the tomography image displayed on the display unit 106, goes through a central part of the treatment region R and is also contained within an area having body tissues of the examined subject P. The straight line is set so as to extend parallel to the Y-Y' axis shown in FIG. 5A, i.e., so as to extend parallel to the y-axis shown in FIG. 5A.

When the thickness of the examined subject P is measured, the control unit 100 compares the measured thickness with the height of the center of the treatment region R that is set. In FIG. 5A, the thickness of the examined subject P is expressed as P5, whereas the height of the center of the treatment region R is expressed as P51. As explained above, because the height of the heated region Q corresponds to the middle point of the standing wave with respect to the y-axis direction, it is necessary to place a pad 600 having a corresponding thickness on the examined subject P, for the purpose of making the treatment region R coincide with the heated region Q. Based on the thickness P5 of the examined subject P and the height P51 of the center of the treatment region R, the control unit 100 calculates a thickness P61 of the pad 600 to be placed, displays the calculated thickness P61 on the display unit 106, and prompts the user to place the pad 600 having the thickness P61 on the examined subject P. More specifically, the thickness P61 of the pad 600 is calculated so that a half of the sum of the height of the examined subject P and the height of the pad 600 coincides with the height of the treatment region R. In other words, the thickness P61 is calculated by using the following condition expression: $2 \times P51 = P5 + P61$.

Further, together with the calculation of the thickness P61 of the pad 600, the control unit 100 also calculates the wavelength of a heating pulse to be radiated onto the examined subject P. More specifically, the wavelength of the heating pulse is calculated in such a manner that a wavelength $\lambda$ of the heating pulse within the body tissues of the examined subject P is twice as large as the sum of the height of the examined subject P and the height of the pad 600. In other words, the wavelength $\lambda$ of the heating pulse within the body tissues of the examined subject P is calculated by using the following condition expression: $\lambda = (P5 + P61) \times 2$.

In FIG. 5B, a manner in which the pad 600 is placed on the examined subject P, after the examined subject P is moved is shown. When the treatment region R is set, the couchtop control unit 205 moves the couchtop 500 so as to move the examined subject P in such a manner that the coordinates of the treatment region R coincide with the Y-Y' axis on the x-z plane. Further, to cause the coordinates of the heated region Q to coincide with the coordinates of the treatment region R on the y-axis, the control unit 100 displays the required thickness of the pad 600 on the display unit 106 and prompts the user to place the pad 600 on the examined subject P. In addition, the control unit 100 also calculates the wavelength of the heating pulse to be radiated.

When a state shown in FIG. 5B is achieved so that the heated region Q coincides with the treatment region R, the control unit 100 displays information on the display unit 106 indicating that the heated region Q coincides with the treatment region R and that a heat treatment should be started. The user acknowledges the display on the display unit 106 and inputs an instruction to start the heat treatment by using the input unit 107.

When the instruction to start the heat treatment is input through the input unit 107, the control unit 100 starts the temperature measuring process and the body movement measuring process, together with the heating process performed on the examined subject P. More specifically, the interface control unit 101 outputs control signals to the heating coil control unit 204, to the gradient magnetic field power source 201, and to the high-frequency transmission coil control unit

202. The heating coil control unit 204 exercises control so that the heating coil 400 radiates a heating pulse onto the examined subject P. Further, the gradient magnetic field power source 201 operates so that the gradient magnetic field coils 301 apply a gradient magnetic field to the examined subject P. Also, the high-frequency transmission coil control unit 202 exercises control so that the high-frequency transmission coil 303 transmits an RF wave to the examined subject P. The image processing unit 102 receives a magnetic resonance signal from the examined subject P, generates a tomography image, which is a transverse-relaxation-period-weighted image, and outputs the generated tomography image to the temperature measurement processing unit 103 and to the body movement measurement processing unit 104. The temperature measurement processing unit 103 sets a tomography image taken immediately before the heating pulse is radiated as a reference image, generates a temperature change image based on the tomography image being output from the image processing unit 102 and on the reference image, and outputs the generated temperature change image to the storage unit 105 or to the display unit 106. The body movement measurement processing unit 104 sets the same image as set by the temperature measurement processing unit 103 as a reference image, generates a body movement image based on the tomography image being output from the image processing unit 102 and on the reference image, and outputs the generated body movement image to the storage unit 105 or to the display unit 106.

Immediately before the heating coil 400 starts radiating the heating pulse, the control unit 100 generates one or more tomography images of the examined subject P, so that the temperature measurement processing unit 103 and the body movement measurement processing unit 104 are able to generate the reference image, based on the one or more tomography images generated immediately before the radiation of the heating pulse.

Figure 6:
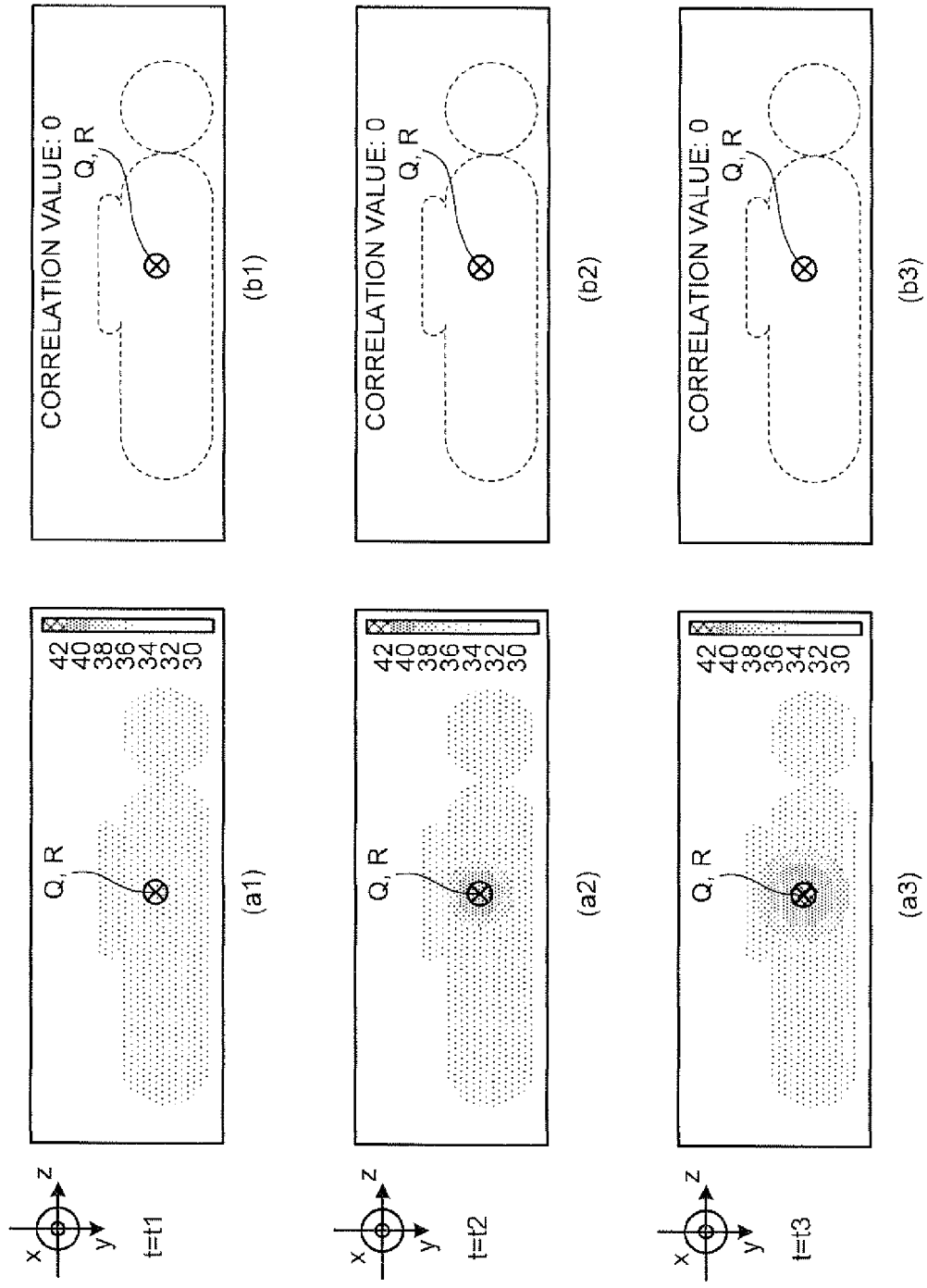
FIG. 6 is a drawing of examples in which a temperature change image and a body movement image are displayed, according to the embodiment.

In FIG. 6, changes over the course of time in the temperature change image generated by the temperature measurement processing unit 103 and in the body movement image generated by the body movement measurement processing unit 104 are shown. FIGS. 6(*a*1), 6(*a*2), and 6(*a*3) illustrate temporal changes in the temperature change image, whereas FIGS. 6(*b*1), 6(*b*2), and 6(*b*3) illustrate temporal changes in the body movement image. To simplify the explanation with reference to FIG. 6, let us assume that temperature of the body tissues of the examined subject P and the temperature of the pad 600 are uniform when the heating pulse is not being radiated. Let us also assume that the examined subject P has no body movement between a time t1 and a time t3.

To make it easy to understand the positional relationship between the heated region Q and the treatment region R, the control unit 100 causes the display unit 106 to display markers indicating the positions of the heated region Q and the treatment region R, in such a manner that the markers are superimposed on the temperature change image and on the body movement image, as shown in FIG. 6. In this situation, for example, the control unit 100 displays the heated region Q by calculating the display position of the heated region Q, based on a relative positional relationship between the couchtop 500 and the heating coils 400 and on position information of the cross-sectional plane on which the tomography image was taken. The control unit 100 displays the treatment region R so that the display position of the treatment region R is positioned in an area set by using the input unit 107. The control unit 100 may calculate a body movement amount and a body movement direction based on the body movement image and may display an image after moving the treatment region R in accordance with the calculated body movement amount and the calculated body movement direction.

Further, as shown in FIG. 6(*a*1), the control unit 100 displays, within the temperature change image, a bar that associates pixel values with temperatures of the body tissues.

Further, as shown in FIG. 6(*b*1), the control unit 100 displays, within the body movement image, an index value indicating the body movement amount. Examples of the index value indicating the body movement amount include a correlation value between the reference image and the current tomography image.

Furthermore, to make it easy to understand the display of the body movement image, the control unit 100 displays, within the body movement image, the edge in the tomography image collected at the current time by superimposing a dotted line thereon.

At a time (i.e., the time t1 in FIG. 6(*a*1)) immediately before the heating pulse is radiated, the temperature of the body tissues in the heated region Q is the same as the temperature of other body tissues because no temperature change has occurred. When a certain period of time has elapsed since the radiation of the heating pulse is started (i.e., the time t2 in FIG. 6(*a*2)), the radiated heating pulse applies heat to an area centered around the heated region Q of the examined subject P, so as to raise the temperature of the body tissues. In the temperature change image, the temperature increase is displayed by, for example, making higher the concentration level of the area in which the temperature has risen. When another period of time has elapsed while the heating pulse is being radiated (i.e., the time t3 shown in FIG. 6(*a*3), the radiated heating pulse further raises the temperature of the heated region Q of the examined subject P. If the examined subject P has no body movement, because the outline of the examined subject P does not change, no outline is displayed in the body movement image for the reason that a subtraction is calculated between the edge in the reference image and the edge in the current-time tomography image.

By monitoring the temperature change image that changes over the course of time, the user recognizes the temperature changes in the body tissues in the treatment region R and in the surroundings of the treatment region R. Also, by monitoring the body movement image that changes over the course of time, the user recognizes the manner in which body movements of the examined subject P occur. On the display unit 106, the temperature change image and the body movement image may be displayed at the same time while being arranged on one screen. Alternatively, the displayed view may be switched between the temperature change image and the body movement image, based on an input via the input unit 107. As another alternative, it is also acceptable to omit the display of the temperature change image or the display of the body movement image and to cause the display unit 106 to display, instead, the temperature of the treatment region R or the index value indicating the body movement amount.

Detection of the Body Movements of the Examined Subject

Figure 7:
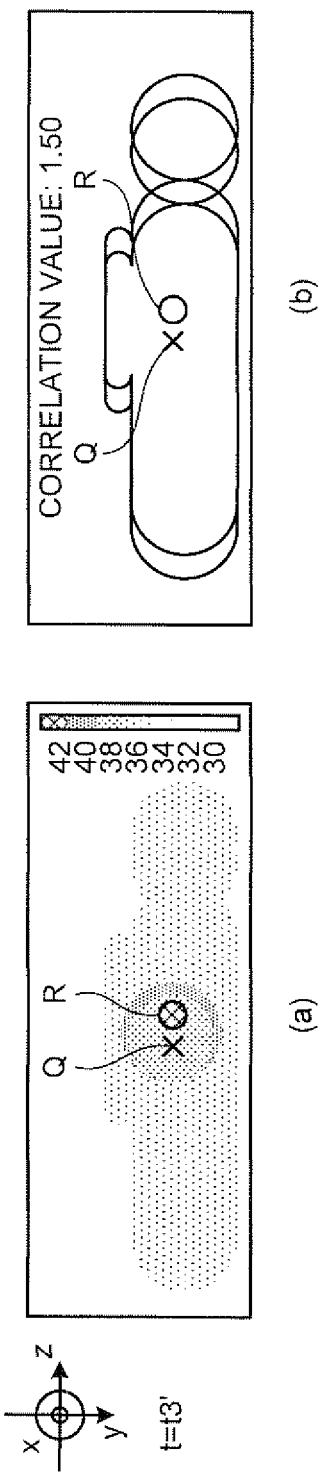
FIG. 7 is a drawing of examples in which a temperature change image and a body movement image are displayed while a body movement occurs, according to the embodiment.

In the explanation above, it is assumed that the examined subject P has no body movement; however, during an actual heat treatment, there is a possibility that a body movement occurs and the examined subject P moves. In FIGS. 7(*a*) and 7(*b*), a temperature change image and a body movement image that are obtained when the examined subject P has a body movement at a time t3' are shown. In FIG. 7, it is assumed that the examined subject P moves in the +z direction shown in the drawings.

If the examined subject P moves in the +z direction, the impact of the movement appears in the body movement image. In other words, because the position of the edge obtained when the reference image was generated is different from the position of the edge in the current image, the pixel values are not cancelled out by the subtraction. As a result, the edge is displayed double in the body movement image. In conjunction with this, the index value for body movements displayed in the body movement image also changes. When a correlation value is used as the index value, the larger the body movement amount is, the smaller is the correlation value being displayed.

The control unit 100 calculates a moving amount and a moving direction of the examined subject P and moves the markers indicating the treatment region R and being displayed in the temperature change image and in the body movement image. As a result, in these two images, the markers are displayed while the position of the marker indicating the treatment region R is different from the position of the marker indicating the heated region Q.

When the position of the heated region Q is different from the position of the treatment region R, the heat will be applied to some of the body tissues (i.e., normal body tissues) other than the body tissues in the affected site. To avoid this situation, when the user recognizes that the position of the marker indicating the treatment region R is different from the position of the marker indicating the heated region Q in the temperature change image or in the body movement image, the user inputs a control signal to stop the heating process by using the input unit 107. When the control unit 100 receives the control signal to stop the heating process, the control unit 100 stops the output of the control signal that instructs the heating pulse radiation and that is output from the interface control unit 101 to the heating coil control unit 204. As a result of this operation, the radiation of the heating pulse by the heating coils 400 onto the examined subject P is stopped, so that the heating processed performed on the body tissues is stopped.

In the example described above, the operation to stop the radiation of the heating pulse is triggered by an input by the user through the input unit 107; however, it is also acceptable to configure the control unit 100 so as to automatically perform the operation to stop the heating pulse radiation by detecting a body movement of the examined subject P based on the body movement image or the temperature change image.

To detect a body movement of the examined subject P by using the body movement image, the control unit 100 monitors the index value indicating the body movements. When judging that the index value indicating the body movements has changed so as to exceed a predetermined threshold value, the control unit 100 determines that the examined subject P has had a significant body movement and stops the radiation of the heating pulse.

To detect a body movement of the examined subject P by using the temperature change image, the control unit 100 monitors the temperature of the body tissues of the examined subject P. When judging that the temperature of any body tissue other than those in the treatment region R has exceeded a predetermined threshold value, the control unit 100 determines that, due to a body movement of the examined subject P, the heated region Q has moved to a position different from the position of the treatment region R and that heat is being applied to normal body tissues. Thus, the control unit 100 stops the radiation of the heating pulse.

Alternatively, another arrangement is acceptable in which the control unit 100 monitors a relative positional relationship between the marker indicating the heated region Q and the marker indicating the treatment region R that are displayed in the body movement image or the temperature change image. In that situation, when the distance between the two markers has exceeded a predetermined threshold value, the control unit 100 determines that the treatment region R has moved due to a body movement of the examined subject P and stops the radiation of the heating pulse.

By performing the operations described above, the control unit 100 causes the temperature change image and the body movement image to be displayed in such a manner that it is possible to monitor the body movements of the examined subject P. By stopping the radiation of the heating pulse in response to the body movements of the examined subject P, it is possible to prevent the heating process from being performed on the normal body tissues of the examined subject P.

Controlling the Heating Pulse Radiation Timing in Synchronization with Respiration In the sections above, the operation to stop the radiation of the heating pulse in response to the body movement of the examined subject P is explained; however, the body movements of the examined subject P include not only temporary body movements, but also body movements that periodically occur, such as those associated with pulsation and/or respiration.

Figure 8:
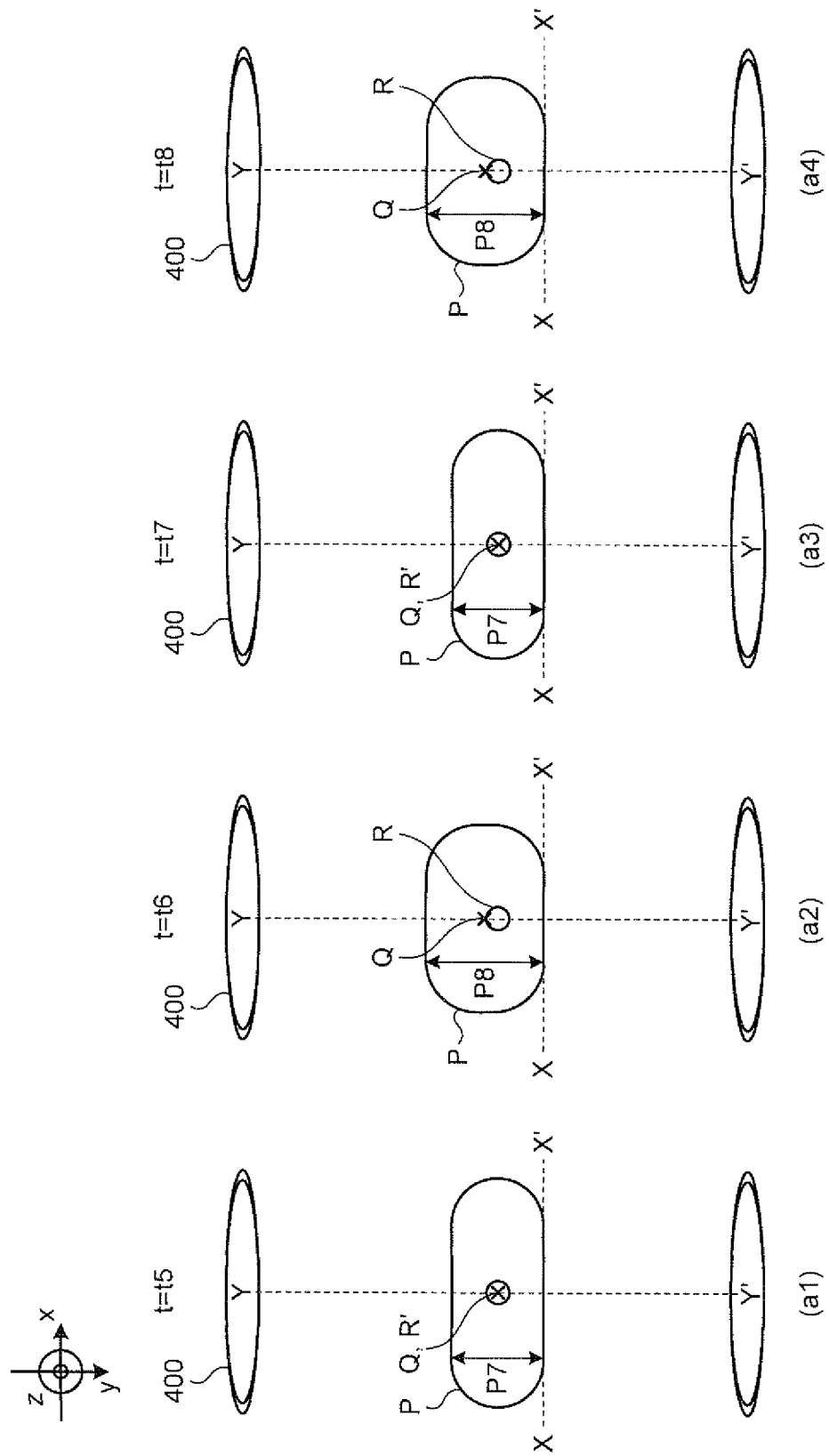
FIG. 8 is a drawing of examples of periodic body movements according to the embodiment.

In FIG. 8, the manner in which periodical body movements occur in the examined subject P is shown. For example, when a focus is placed on the x-y plane, the chest and the like of the examined subject P moves up and down in synchronization with respiration. Because the cycle of respiration is substantially regular, the state in which the chest of the examined subject P down (FIGS. 8(a1) and 8(a3)) and the state in which the chest of the examined subject P is up (FIGS. 8(a2) and 8(a4)) alternate periodically. More specifically, the time interval (t7-t5) between FIG. 8(a1) and FIG. 8(a3) is substantially equal to the time interval (t8-t6) between FIG. 8(a2) and FIG. 8(a4).

As explained above, the position of the treatment region R moves according to body movements of the examined subject P. When a body movement periodically occurs in the examined subject P, and also, the position of the heated region Q and the position of the treatment region R coincide with each other at certain points in time during the periodical movements, the times at which the heated region Q and the treatment region R coincide with each other also come periodically. For this reason, the magnetic resonance diagnostic apparatus 1 according to the present embodiment is configured in such a manner that the control unit 100 exercises control so that the heating pulse is radiated in synchronization with the times, which come periodically, at which the heated region Q and the treatment region R coincide with each other. More specifically, the control unit 100 exercises control so that tomography images of the examined subject P are successively generated for a certain period of time between the time at which the treatment region R finishes being set and the time at which the heating pulse starts being radiated. The image processing unit 102 selects one of the plurality of tomography images collected during the certain period of time and calculates a correlation value between the selected tomography image and each of the other tomography images. If the shape of the examined subject P periodically changes, when the calculated correlation values are associated with the times at which the tomography images are collected, it is observed that the correlation values increase and decrease in synchronization with the cycle of the periodical changes. Based on the cycle of the periodical changes in the correlation values, the control unit 100 calculates a time interval ΔT of the body movements of the examined subject P.

Figure 9:
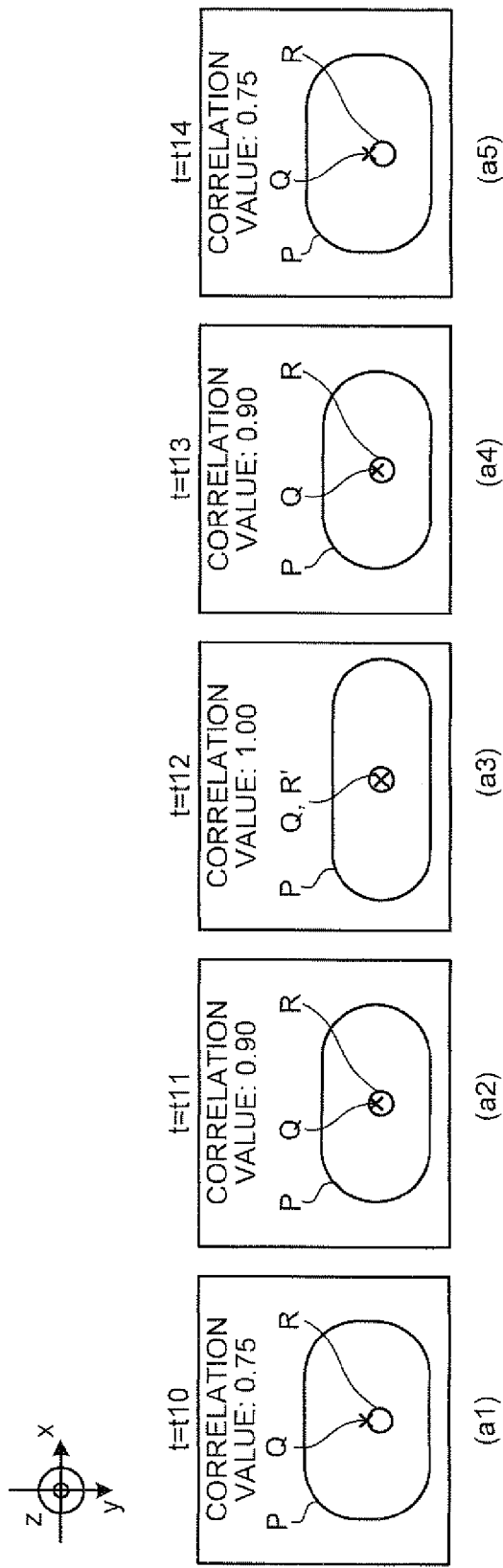
FIG. 9 is a drawing of a series of body movement images extracted according to the embodiment.

When the cycle of the periodical changes of the body movements is calculated, the control unit 100 subsequently calculates a time period Δt during which the heated region Q and the treatment region R overlap each other. More specifically, the control unit 100 selects, out of the plurality of tomography images being collected, a tomography image having a high level of correlation (i.e., a tomography image showing an identical shape of the examined subject P) with the tomography image used for setting the treatment region R. When the one tomography image is selected, the control unit 100 extracts a plurality of tomography images that were taken at times close to the time (hereinafter, a "center time") at which the selected tomography image was taken and causes the display unit 106 to display the extracted tomography images on one screen. When the extracted tomography images are displayed, the image processing unit 102 adds the markers indicating the heated region Q and the treatment region R to each of the extracted tomography images. In FIG. 9, examples of the display of the tomography images on the display unit 106 are shown. In FIG. 9, the center time is expressed as t12, and the tomography image used for setting the treatment region R is shown in FIG. 9(a3). As shown in FIG. 9, the control unit 100 may display the calculated correlation values, together with the tomography images being displayed.

When the time (hereinafter, "tomography image collection time") at which each of the extracted plurality of tomography images was taken is sufficiently close to the center time t12, the following is observed: the farther the tomography image collection time is from the center time t12, the larger is the body movement amount in comparison with the state shown in FIG. 9(a3). In this situation, as the body movement amount becomes larger, the difference amount between the positions of the heated region Q and the treatment region R also becomes larger gradually. By selecting a number of tomography images out of the tomography images that are displayed on one screen, the user sets a time period Δt during which the positional difference between the heated region Q and the treatment region R is tolerable. More specifically, if the user judges that the heated region Q and the treatment region R overlap each other in the tomography images shown in FIGS. 9(a2), 9(a3), and 9(a4), the user selects the tomography images shown in FIGS. 9(a2), 9(a3), and 9(a4), by using the input unit 107. Upon receipt of the input, the control unit 100 calculates the time period Δt during which the heated region Q and the treatment region R are judged to overlap each other, based on the tomography image collection times at which the tomography images shown in FIGS. 9(a2) to 9(a4) were taken. In the example shown in FIGS. 9(a2) to 9(a4), the time period Δt is obtained by calculating t13−t11=Δt.

In the present embodiment, the example is explained in which the time period Δt is calculated by selecting the tomography images based on the input through the input unit 107; however, the method for calculating the time period Δt is not limited to this example. For example, another arrangement is acceptable in which the user determines, in advance, a threshold value for the correlation value by using the input unit 107, so that the control unit 100 calculates a time period during which the correlation value is larger than a predetermined level while using the center time as the center and determines the calculated time period as the time period Δt. Alternatively, yet another arrangement is acceptable in which the user directly specifies the value of the time period Δt by using the input unit 107.

When having calculated the time interval ΔT of the body movements of the examined subject P, as well as the time period Δt during which the heated region Q and the treatment region R overlap each other, the control unit 100 predicts a time at which the heated region Q and the treatment region R overlap each other, based on the time interval ΔT and the time period Δt. In other words, when the heated region Q and the treatment region R overlap each other at a point in time (e.g., the time t12), the control unit 100 predicts the time (e.g., a time t15) at which the heated region Q and the treatment region R overlap each other again by calculating t15=t12+ΔT.

Figure 10:
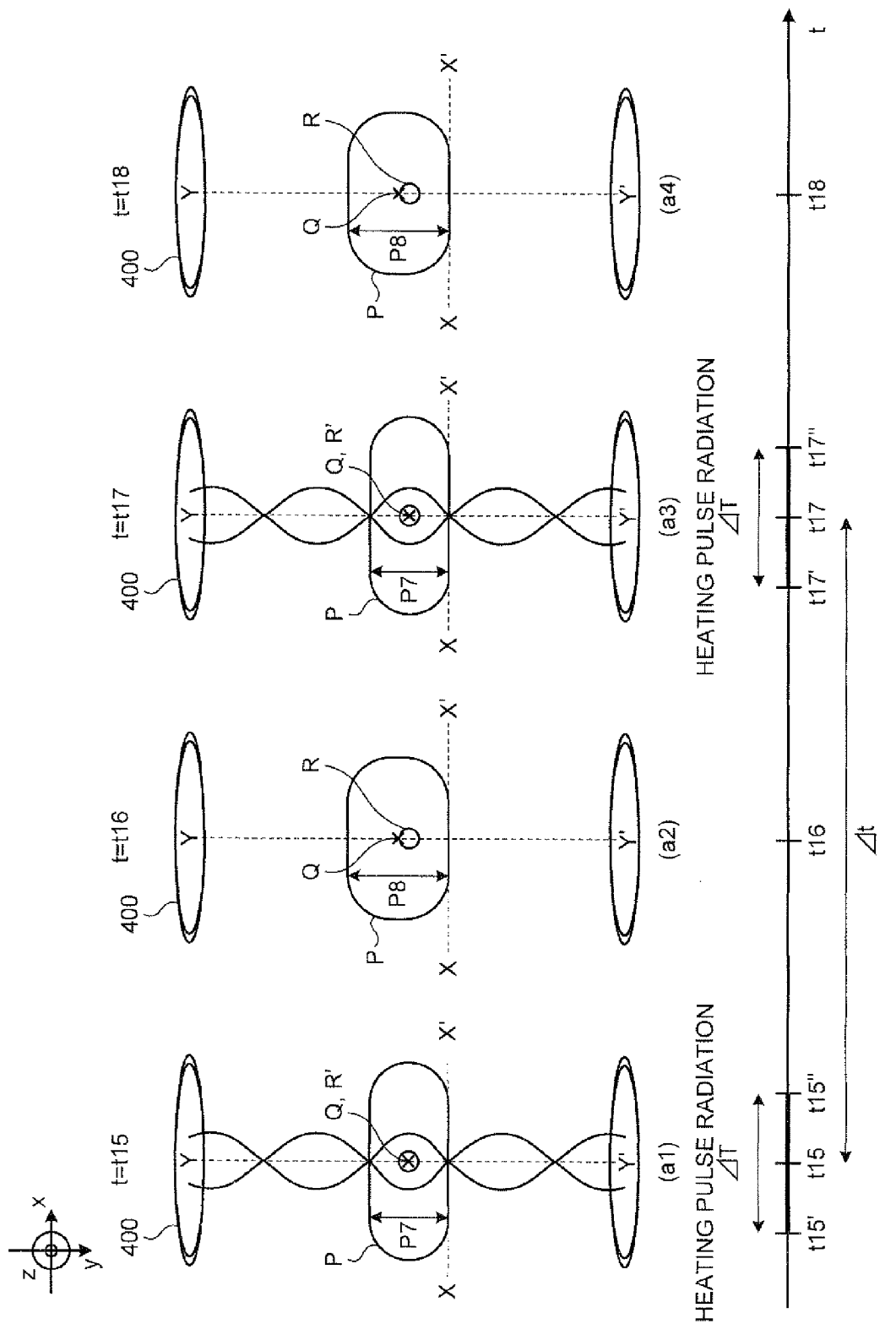
FIG. 10 is a drawing for explaining a manner in which heating pulse radiation periods are controlled in synchronization with body movement cycles according to the embodiment.

When having predicted the time at which the heated region Q and the treatment region R overlap each other again, the control unit 100 controls the heating coil control unit 204 so that the heating pulse is radiated only during the time period equal to Δt, while using the predicted time as the center of the time period. In FIG. 10, a manner in which the control unit 100 controls the radiation periods of the heating pulse in synchronization with periodical body movements of the examined subject P is shown. When the control unit 100 predicts that the time at which the heated region Q and the treatment region R overlap each other again is the time t15, the heating coil control unit 204 stops the radiation of the heating pulse until a time t15', which can be calculated by the following expression: t15−Δt=t15'. At the time t15', the heating coil control unit 204 resumes and continues the radiation of the heating pulse until a time t15", which can be calculated by the following expression: t15+Δt=t15". At t15", the heating coil control unit 204 stops the radiation of the heating pulse again. Subsequently, the control unit 100 calculates another time (e.g., a time t17) at which the heated region Q and the treatment region R overlap each other again by using the expression t15+ΔT=t17. The heating coil control unit 204 then radiates the heating pulse during the time period from t17' to t17" by using the time t17 as a reference.

As a result of the control described above, the control unit 100 detects the periodical body movements of the examined subject P and calculates the cycle of the body movements. Further, the control unit 100 sets the time period during which the heated region Q and the treatment region R overlap each other. The heating coil control unit 204 predicts the times at each of which the heated region Q and the treatment region R overlap each other and arranges the heating pulse to be radiated at those times. With these arrangements, even if the body movements occur in the examined subject P, it is possible to predict the shifting of the treatment region R and to radiate the heating pulse and perform the heating process only at such times when the heat is applied to the treatment region R.

Providing the RP Shields

As explained above, to take the tomography images of the examined subject P, the high-frequency transmission coil 303 radiates the electromagnetic wave towards the examined subject P. The electromagnetic wave radiated from the high-frequency transmission coil 303 includes components that oppose each other: one component propagates from the high-frequency transmission coil 303 toward the inside of the patient bore, whereas the other component propagates from the high-frequency transmission coil 303 toward the outside of the patient bore. In this situation, when a focus is placed on the electromagnetic wave that propagates toward the outside of the patient bore (hereinafter, the magnetic field component of the electromagnetic wave propagating toward the outside of the patient bore will be simply referred to as a "leakage magnetic field"), the leakage magnetic field generates an eddy current on electrically-conductive members such as the gradient magnetic field coils 301 and the magnetostatic field magnet 300 that are positioned outside the high-frequency transmission coil 303, a thermal shield that shields the magnetostatic field magnet 300, and the like. Because the eddy current generates a magnetic flux in such a direction that cancels out the magnetic field component of the electromagnetic wave propagating toward the inside of the patient bore, it becomes impossible, as a result, to sufficiently apply the magnetic field component onto the examined subject P.

Figure 11:
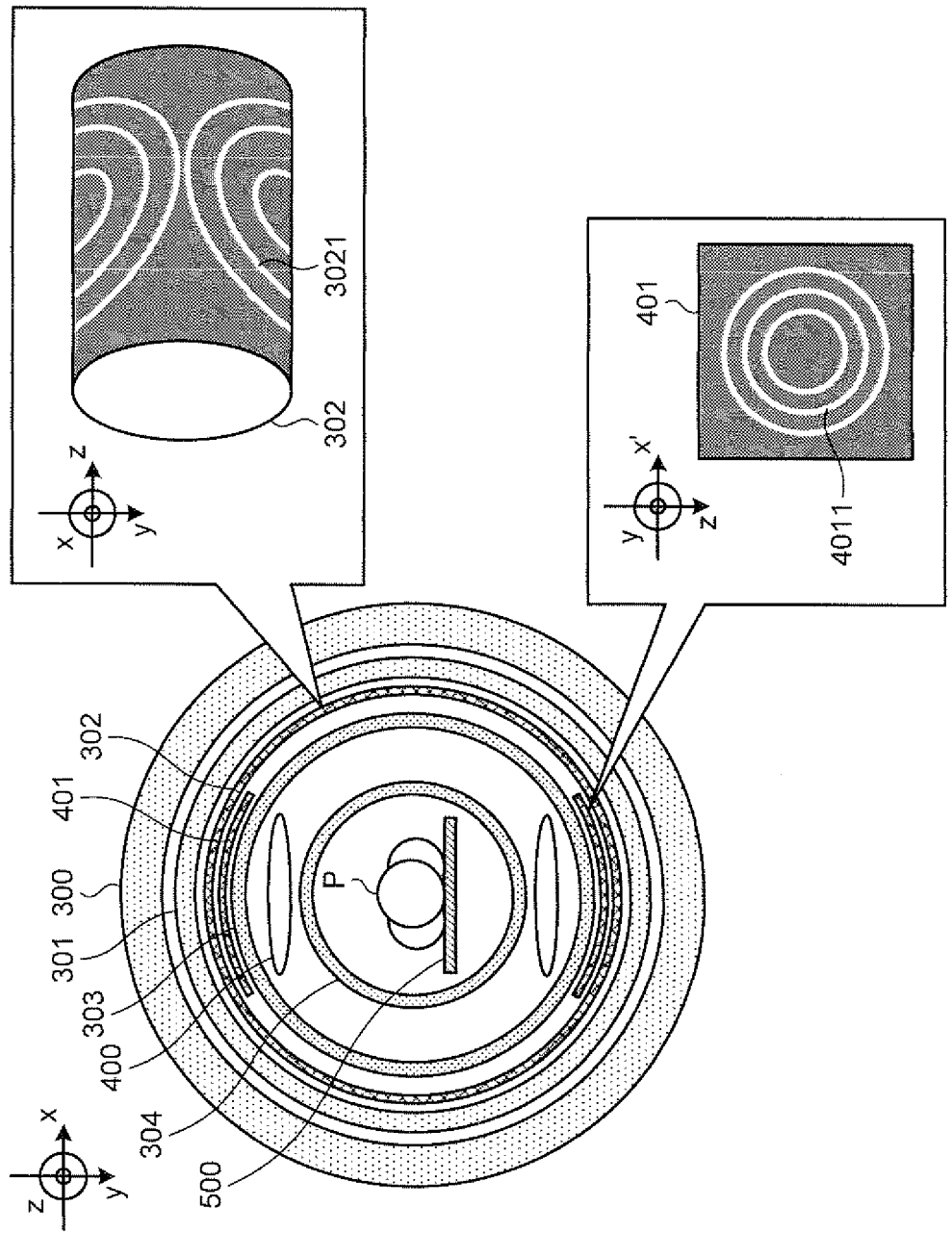
FIG. 11 is a drawing of heating coil RF shields according to the embodiment.

To inhibit the impact of the leakage magnetic field as described above, the transmission coil RF shield 302 is provided between the high-frequency transmission coil 303 and the gradient magnetic field coils 301. In FIG. 11, an exemplary configuration of the transmission coil RF shield 302 is shown. The transmission coil RF shield 302 may be, for example, configured with an electrically-conductive material such as copper or aluminum and is configured in the form of a circular cylinder that surrounds the high-frequency transmission coil 303. Also, slits 3021 each having a circular shape are provided in the high-frequency transmission coil 303. For example, the slits 3021 are provided so as to draw circles centered on an arbitrary axis perpendicular to the z-axis, i.e., centered on an axis perpendicular to the radiation axis of the RE pulse transmitted by the high-frequency transmission coil 303. The leakage magnetic field caused by the RE pulse transmitted by the high-frequency transmission coil 303 generates an eddy current in the form of circles centered on an axis perpendicular to the z-axis, on the transmission coil RE shield 302, which is an electrically-conductive member. The circular-shaped slits 3021 provided in the direction perpendicular to the z-axis, however, do not block the path of the eddy current. Because the eddy current generated by the RE pulse transmitted by the high-frequency transmission coil 303 generates a magnetic flux in such a direction that cancels out the leakage magnetic field, the leakage magnetic field is, as a result, cancelled out, so that the magnetic field component advances toward the examined subject P.

Next, a focus will be placed on the leakage magnetic field caused by the heating coils 400. When the heating process is performed on the examined subject P, the heating coil 400 radiates the heating pulse toward the examined subject P. The heating pulse radiated from the heating coil 400 includes components that oppose each other: one component propagates from the heating coil 400 toward the inside of the patient bore, whereas the other component propagates from the heating coil 400 toward the outside of the patient bore. Thus, like in the example of the high-frequency transmission coil 303, a leakage magnetic field is caused. To inhibit the impact of the leakage magnetic field caused by the heating pulse, each of the heating coil RF shields 401 is provided between a different one of the heating coils 400 and the high-frequency transmission coil 303. In FIG. 11, an exemplary configuration of the heating coil RF shields 401 is shown. Like the transmission coil RF shield 302, the heating coil RF shields 401 may be configured with an electrically-conductive material such as copper or aluminum. For the purpose of receiving the leakage magnetic field caused by the heating coils 400, the heating coil RF shields 401 are obtained by, for example, bending rectangular-shaped plate-like members each having a larger area than the area of the heating coil 400 with respect to the x-axis shown in FIG. 11, in such a manner that each of the heating coil RF shields 401 can be inserted between the transmission coil RF shield 302 and the high-frequency transmission coil 303.

Further, slits 4011 each having a circular shape are provided in the heating coil RF shields 401. For example, the slits 4011 are provided so as to draw circles centered on an axis perpendicular to the y-axis, i.e., centered on an axis perpendicular to the radiation direction of the heating pulse. The leakage magnetic field caused by the heating pulse generates an eddy current flowing in the form of circles centered on an axis perpendicular to the y-axis, on the heating coil RF shields 401. The circular-shaped slits 4011 provided in the direction perpendicular to the y-axis, however, do not block the path of the eddy current. Because the eddy current flowing on the heating coil RF shields 401 generates a magnetic flux in such a direction that cancels out the leakage magnetic field caused by the heating pulse, the leakage magnetic field is, as a result, cancelled out, so that the magnetic field component advances toward the examined subject P.

By providing the heating coil RF shields 401, it is possible to cancel out the leakage magnetic field caused by the heating pulse and to arrange the energy of the electromagnetic wave to be concentrated on the examined subject P, so as to be able to perform the heating process on the examined subject P more efficiently. Further, it is also possible to avoid the situation where the leakage magnetic field generates eddy currents on the gradient magnetic field coils 301, the magnetostatic field magnet 300, and the thermal shield that are provided on the outside of the heating coil RF shields 401.

In addition, the leakage magnetic field caused by the RF pulse transmitted from the high-frequency transmission coil 303 also flows into the heating coil RF shields 401. The leakage magnetic field caused by the RF pulse transmitted from the high-frequency transmission coil 303 generates an eddy current in the form of circles centered on an axis perpendicular to the z-axis, on the heating coil RF shields 401. The flowing direction of this eddy current, however, is blocked by the slits 4011 that are provided while being centered on the axis perpendicular to the y-axis. In other words, on the heating coil RF shields 401, no eddy current is generated by the RF pulse transmitted from the high-frequency transmission coil 303. Because no impact is made by eddy currents, the heating coil RF shields 401 are substantially negligible in the viewpoint of the high-frequency transmission coil 303.

As explained above, the transmission coil RF shield 302 and the heating coil RF shields 401 are provided between the high-frequency transmission coil 303 and the gradient magnetic field coils 301. The transmission coil RF shield 302 is able to cancel out the leakage magnetic field caused by the RF pulse transmitted by the high-frequency transmission coil 303. Also, the heating coil RF shields 401 are able to cancel out the leakage magnetic field caused by the heating pulse. Further, because the slits 3021 and the slits 4011 are provided in the directions that are orthogonal to each other, it is possible to reduce the impact on the heating coil RF shields 401 from the leakage magnetic field caused by the RF pulse transmitted by the high-frequency transmission coil 303.

Other Configurations of the Heating Coils 400

In the description of the exemplary embodiment above, the example is explained in which the heating coils 400 are disposed, as shown in FIG. 1, between the high-frequency transmission coil 303 and the high-frequency reception coil 304 so as to be positioned above and below the heated region Q (i.e., in mutually-different positions on the y-axis in common, respectively). However, the configuration of the heating coils 400 is not limited to this example. Other exemplary configurations of the heating coils 400 will be explained below.

Figure 12:
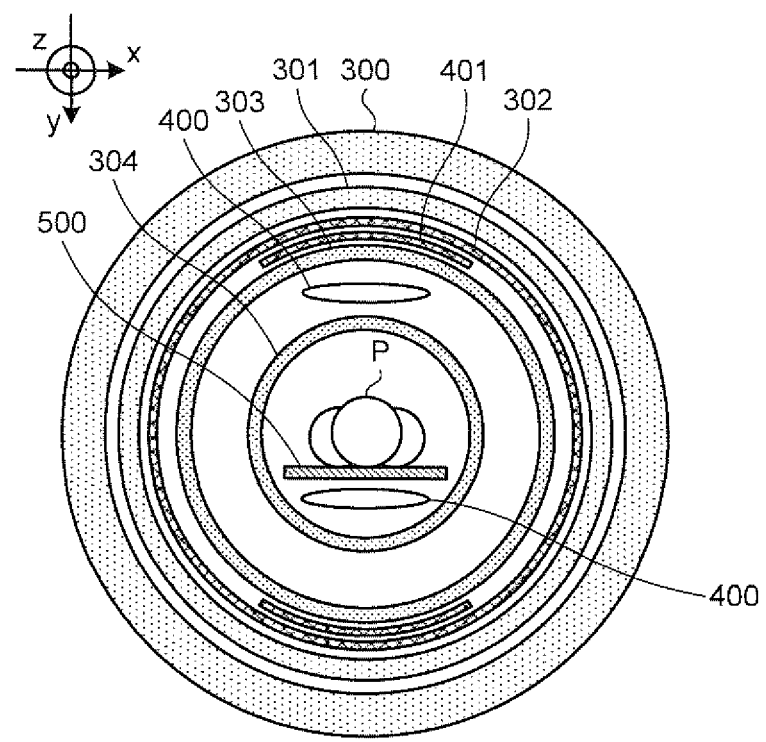
FIG. 12 is a drawing of another configuration of the heating coils according to another embodiment.

In FIG. 12, an example in which one of the heating coils 400 is disposed within the couchtop 500 is shown. The heating coil 400 is, for example, attached as being fixed onto an internal wall (not shown) provided on the inside of the high-frequency reception coil 304. As shown in FIG. 12, it is acceptable to attach the heating coils 400 in positions that are asymmetrical with respect to the heated region Q. Because the lower heating coil 400 is positioned closer to the examined subject P, the heating pulse is radiated onto the body tissues of the examined subject P before diffusing. Because the amount of the heating pulse diffusing into the air is smaller, it is possible to efficiently perform the heating process on the examined subject P by using a smaller amount of energy of the heating pulse.

Figure 13B:
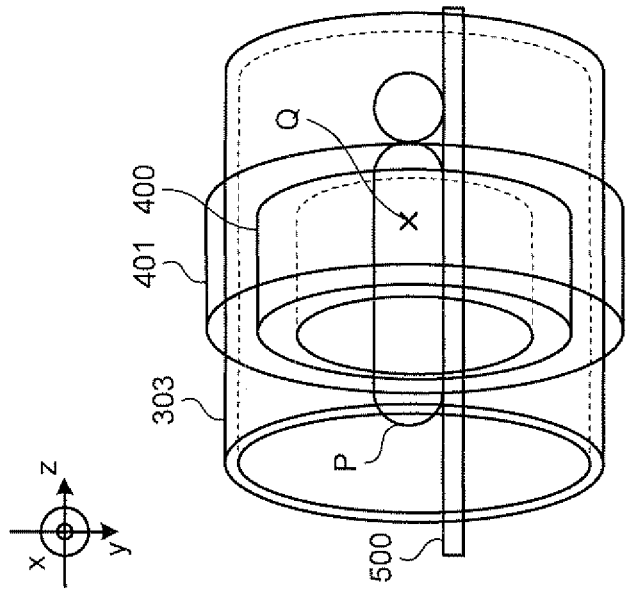
FIGS. 13A and 13B are drawings of yet another configuration of a heating coil and a heating coil RF shield according to yet another embodiment.
Figure 13A:
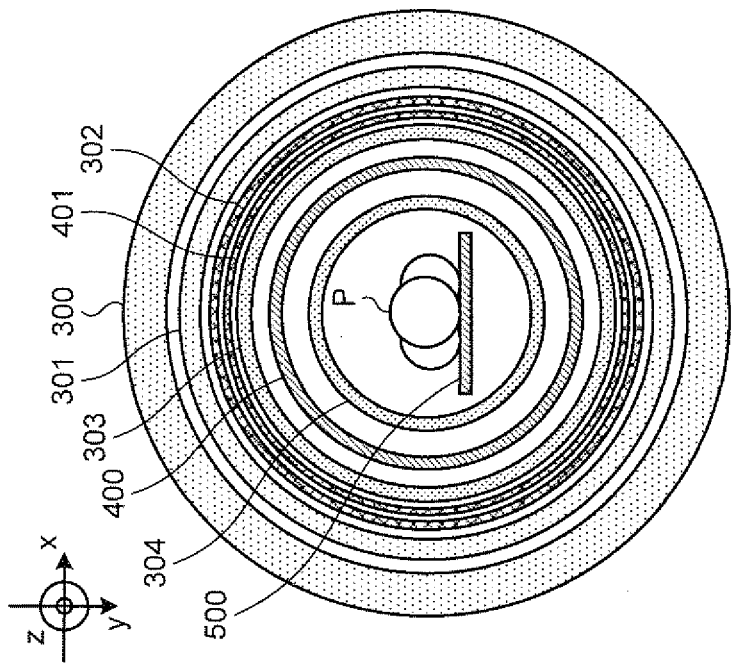

In FIGS. 13A and 13B, an example in which a heating coil 400 is configured in the form of a circular cylinder is shown. FIG. 13A is a drawing of the heating coil 400 viewed on a plane perpendicular to the body axis of the examined subject P. FIG. 13B is a drawing of the heating coil 400 and a heating coil RF shield 401 viewed from a lateral side of the examined subject P. As shown in FIGS. 13A and 13B, it is acceptable to configure the heating coil 400 in the form of a circular cylinder that surrounds the body axis of the examined subject P. In that situation, the heating coil 400 is provided between the high-frequency transmission coil 303 and the high-frequency reception coil 304. It should be noted, however, that as shown in FIG. 13B, the length of the heating coil 400 in the z-axis direction is arranged to be shorter than those of the high-frequency transmission coil 303 and the examined subject P. More specifically, the heating coil 400 is configured so as to be approximately 10 centimeters to 30 centimeters long in the z-axis direction. When the heating coil 400 is configured in the form of a circular cylinder, the heating coil RF shield 401 that absorbs the leakage magnetic field caused by the heating coil 400 is configured in the form of a circular cylinder that surrounds the heating coil 400. In the present embodiment, the example is shown in which the length of the heating coil RF shield 401 in the z-axis direction is shorter than that of the high-frequency transmission coil 303; however, to absorb more of the leakage magnetic field, another arrangement is acceptable in which the length of the heating coil RF shield 401 is arranged so as to be similar to or longer than the length of the high-frequency transmission coil 303. When the heating coil 400 is configured in the form of a circular cylinder, because the electrically-conductive members are equally disposed on the y-z plane, it is possible to cause the magnetostatic field magnet 300 to generate the magnetic field more evenly.

In this situation, even when the heating coil 400 is configured in the form of a circular cylinder that surrounds the body axis of the examined subject P, the heating coil 400 receives the electric signal being output from the heating coil control unit 204 and radiates the electromagnetic wave onto the examined subject P. It should be noted, however, that the heating coil control unit 204 in this situation controls the phase and the amplitude of the heating pulse supplied to the heating coil 400 in a multi-channel manner so that the energy of the electromagnetic wave is converged into the heated region Q within the examined subject P.

Figure 14:
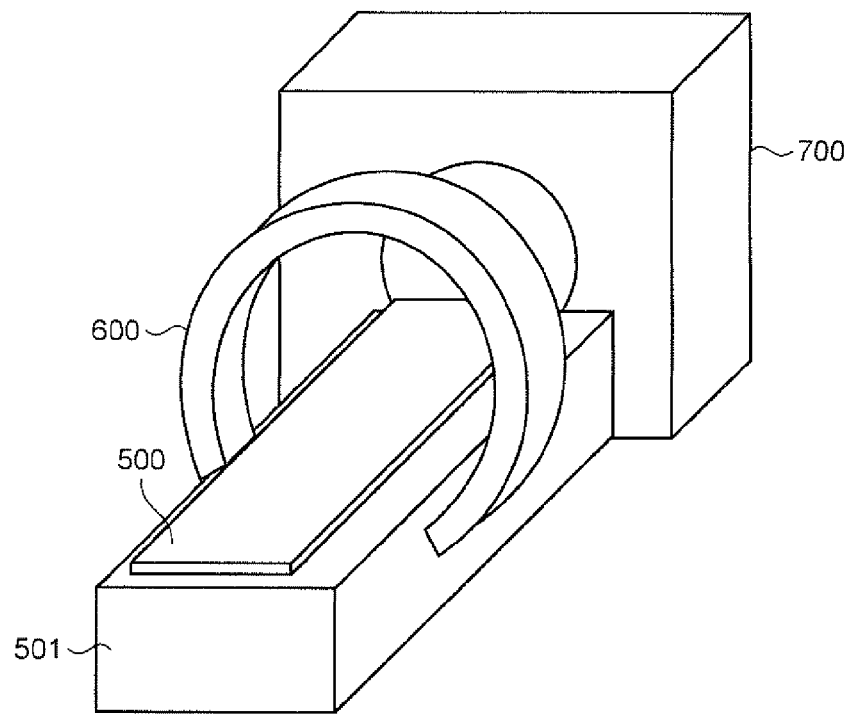
FIG. 14 is a drawing of yet another configuration of a heating coil according to yet another embodiment.
Figure 15:
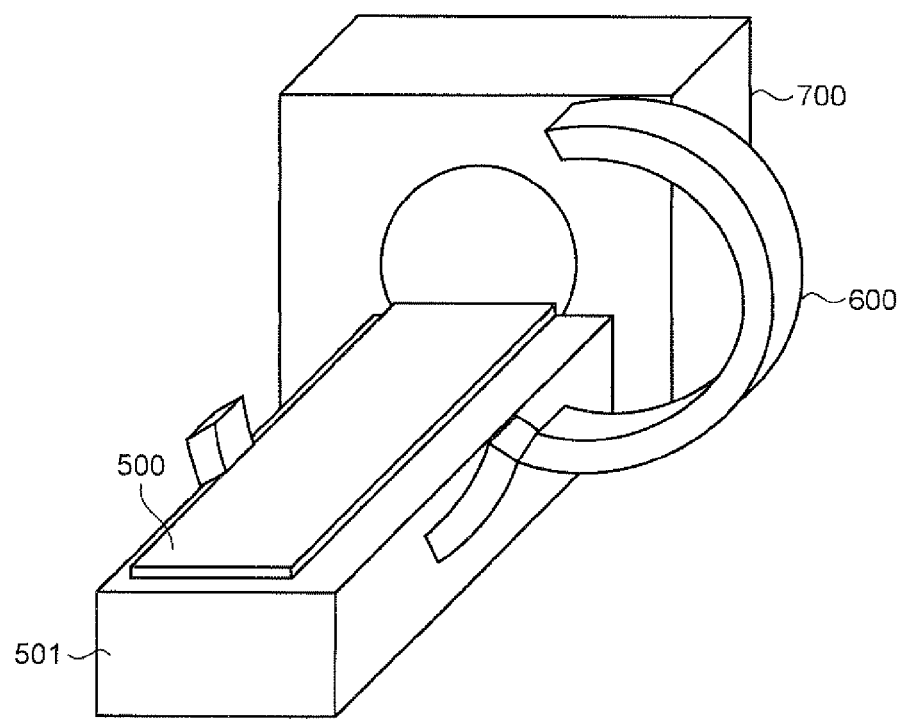
FIG. 15 is a drawing of yet another configuration of the heating coil according to yet another embodiment.

Next, examples in which a heating coil is provided at a couch are shown in FIGS. 14 and 15. A magnetic resonance diagnostic apparatus shown in FIG. 14 includes the couchtop 500, a couch 501, a heating coil 600, and a staging device 700. The staging device 700 includes the magnetostatic field magnet 300, the gradient magnetic field coils 301, the high-frequency transmission coil 303, the high-frequency reception coil 304, and the like that are explained in the exemplary embodiment described above.

The heating coil 600 shown in FIG. 14 is configured in the form of a circular cylinder that surrounds the body axis of the examined subject P. The couch 501 is provided with the heating coil 600. In this situation, under the control of the couchtop control unit 205, the couchtop 500 can be inserted into and carried out of the patient bore provided in the staging device 700, while the examined subject P is placed thereon. In other words, the magnetic resonance diagnostic apparatus shown in FIG. 14 is configured so that the RF wave is transmitted to the examined subject P by the high-frequency transmission coil 303 while the couchtop 500 is inserted in the patient bore provided in the staging device 700, whereas the electromagnetic wave is radiated onto the examined subject P by the heating coil 600 while the couchtop 500 is positioned out of the patient bore provided in the staging device 700. According to this embodiment, for example, it is possible to, first, perform a heating process on the examined subject P by causing the heating coil 600 to radiate the electromagnetic wave onto the examined subject P, and subsequently, measure the temperature by inserting the couchtop 500 into the patient bore provided in the staging device 700. Further, by repeating the insertion and the carrying-out of the couchtop 500, it is possible to repeatedly perform the heating process and the temperature measuring process. To facilitate a process to place the examined subject P onto the couchtop 500, the heating coil 600 shown in FIG. 14 may be configured so as to open up as shown in FIG. 15.

Figure 16:
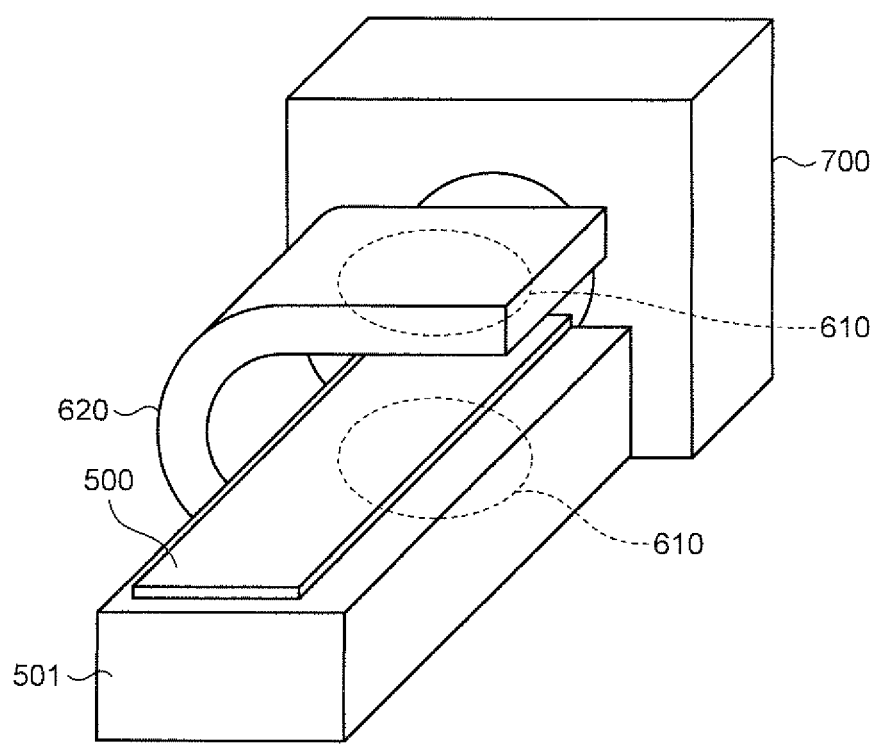
FIG. 16 is a drawing of yet another configuration of a heating coil according to yet another embodiment.

Next, yet another example in which a couch is provided with heating coils is shown in FIG. 16. A magnetic resonance diagnostic apparatus shown in FIG. 16 includes the couchtop 500, the couch 501, a heating coil 610, and the staging device 700.

As shown in FIG. 16, at least one pair of heating coils 610 is provided so as to have the examined subject P interposed therebetween. The couch 501 is provided with the heating coils 610. In this situation, as shown in FIG. 16 for example, a heating coil supporting unit 620 is attached to the couch 501, while one of the pair of heating coils 610 is provided within the heating coil supporting unit 620, whereas the other of the pair is provided within the couch 501 so as to oppose the heating coil 610 provided within the heating coil supporting unit 620.

In this example also, under the control of the couchtop control unit 205, the couchtop 500 can be inserted into and carried out of the patient bore provided in the staging device 700, while the examined subject P is placed thereon. In other words, the magnetic resonance diagnostic apparatus shown in FIG. 16 is configured so that the RF wave is transmitted to the examined subject P by the high-frequency transmission coil 303 while the couchtop 500 is inserted in the patient bore provided in the staging device 700, whereas the electromagnetic wave is radiated onto the examined subject P by the pair of heating coils 610 while the couchtop 500 is positioned out of the patient bore provided in the staging device 700. According to this embodiment, for example, it is possible to, first, perform a heating process on the examined subject P by causing the pair of heating coils 610 to radiate the electromagnetic wave onto the examined subject P, and subsequently, measure the temperature by inserting the couchtop 500 into the patient bore provided in the staging device 700. Further, by repeating the insertion and the carrying-out of the couchtop 500, it is possible to repeatedly perform the heating process and the temperature measuring process. To facilitate a process to place the examined subject P onto the couchtop 500, the heating coil supporting unit 620 shown in FIG. 16 may be configured so as to have an opening as shown in, for example, FIG. 16.

With the arrangements described above, the magnetic resonance diagnostic apparatus 1 according to the exemplary embodiments is configured so that heat is applied to the heated region Q by the heating pulse radiated from the one or more heating coils 400, and also, so that the temperature changes in the examined subject P are measured based on the tomography images. As a result, it is possible to perform the heating process while monitoring the temperature changes in the affected site of the examined subject P. It is therefore possible to perform the heat treatment more efficiently.

Further, the magnetic resonance diagnostic apparatus 1 according to the exemplary embodiments calculates the appropriate wavelength of the heating pulse and the thickness of the pad 600 to be placed, on the examined subject P, based on the tomography images taken and the specified treatment region R. Even if the thickness of the examined subject P is different, because a proper wavelength and a proper thickness of the pad 600 are displayed, it is possible to proceed with the heat treatment efficiently.

Further, the magnetic resonance diagnostic apparatus 1 according to the exemplary embodiments is configured so as to detect movements of the examined subject P based on the tomography images taken and to display a positional difference, if any, between the treatment region R and the heated region Q. With this arrangement, it is possible to prevent the situation where the heat is applied to the normal tissues of the examined subject P, without the possibility of happening.

Further, the magnetic resonance diagnostic apparatus 1 according to the exemplary embodiments is configured so as to detect periodical body movements of the examined subject P such as respiration and to control the times at which the heating pulse is radiated. With this arrangement, it is possible to perform the heating process only at such times when the treatment region R and the heated region Q coincide with each other and to perform the heating process on the treatment region R more efficiently.

Furthermore, the magnetic resonance diagnostic apparatus 1 according to the exemplary embodiments is configured so that the one or more heating coil RF shields 401 are provided on the outside of the heating coils 400. By providing the heating coil RF shields 401 with the slits 4011, it is possible to provide a shield against the leakage magnetic field caused by the heating coils 400, while inhibiting the impact on the high-frequency transmission coil 303 from the heating coil RF shields 401.

It is possible to form various inventions by combining, as appropriate, two or more of the constituent elements disclosed in the exemplary embodiments. For example, it is acceptable to omit one or more of the constituent elements described in any of the exemplary embodiments. Further, it is also acceptable to combine, as necessary, constituent elements from mutually different exemplary embodiments.

By using the magnetic resonance diagnostic apparatus according to an aspect of the described embodiments, it is possible to, at the same time, apply the heat treatment to the examined subject and measure the temperature based on the magnetic resonance signals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance diagnostic apparatus comprising:
a magnetostatic field coil that forms a magnetostatic field;
a gradient coil that superimposes a gradient magnetic field onto the magnetostatic field;
a high-frequency transmission coil that transmits a high-frequency electromagnetic wave at a magnetic resonance frequency to an examined subject placed in the magnetostatic field;
a high-frequency reception coil that receives a magnetic resonance signal transmitted from the examined subject;
an image generating unit that generates a magnetic resonance image of the examined subject, based on the magnetic resonance signal;
a heating coil that performs a heating process by radiating a high-frequency electromagnetic wave onto the examined subject at a frequency different from the magnetic resonance frequency;
a measuring unit that, based on the magnetic resonance signal, measures a temperature of the examined subject changing due to the high-frequency electromagnetic wave radiated by the heating coil; and
a control unit that exercises control so that the measuring unit measures the temperature while the heating coil is performing the heating process, by ensuring that the transmission of the high-frequency electromagnetic wave by the high-frequency transmission coil and the radiation of the high-frequency electromagnetic wave by the heating coil are performed in parallel.

2. The magnetic resonance diagnostic apparatus according to claim 1, further comprising:
an input unit that receives an input of a treatment region, based on the magnetic resonance image; and
a frequency setting unit that, based on the magnetic resonance image and the treatment region, sets the frequency of the high-frequency electromagnetic wave radiated by the heating coil in such a manner that the high-frequency electromagnetic wave radiated by the heating coil forms a standing wave within the examined subject, wherein
the heating coil radiates the high-frequency electromagnetic wave, based on the frequency set by the frequency setting unit.

3. The magnetic resonance diagnostic apparatus according to claim 1, further comprising:
a display unit that displays a character and/or a shape;
an input unit that receives an input of a treatment region, based on the magnetic resonance image;
a pad that is attached to the examined subject; and
a frequency setting unit that, based on the magnetic resonance image and the treatment region, sets the frequency of the high-frequency electromagnetic wave radiated by the heating coil and a thickness of the pad in such a manner that the high-frequency electromagnetic wave radiated by the heating coil forms, within the examined subject and the pad, a standing wave of which an antinode corresponds to the treatment region, wherein
the display unit displays the thickness of the pad set by the frequency setting unit, and
the heating coil radiates the high-frequency electromagnetic wave, based on the frequency set by the frequency setting unit.

4. The magnetic resonance diagnostic apparatus according to claim 1, wherein the heating coil stops radiating the high-frequency electromagnetic wave, based on temperature information measured by the measuring unit.

5. The magnetic resonance diagnostic apparatus according to claim 2, wherein the heating coil stops radiating the high-frequency electromagnetic wave, based on temperature information measured by the measuring unit.

6. The magnetic resonance diagnostic apparatus according to claim 3, wherein the heating coil stops radiating the high-frequency electromagnetic wave, based on temperature information measured by the measuring unit.

7. The magnetic resonance diagnostic apparatus according to claim 1, wherein the heating coil stops radiating the high-frequency electromagnetic wave, based on at least two magnetic resonance images respectively corresponding to magnetic resonance signals collected at mutually-different predetermined times.

8. The magnetic resonance diagnostic apparatus according to claim 2, wherein the heating coil stops radiating the high-frequency electromagnetic wave, based on at least two magnetic resonance images respectively corresponding to magnetic resonance signals collected at mutually-different predetermined times.

9. The magnetic resonance diagnostic apparatus according to claim 3, wherein the heating coil stops radiating the high-frequency electromagnetic wave, based on at least two magnetic resonance images respectively corresponding to magnetic resonance signals collected at mutually-different predetermined times.

10. The magnetic resonance diagnostic apparatus according to claim 1, wherein the heating coil periodically radiates the high-frequency electromagnetic wave, based on a plurality of magnetic resonance images respectively corresponding to magnetic resonance signals collected during a predetermined time period.

11. The magnetic resonance diagnostic apparatus according to claim 2, wherein the heating coil periodically radiates the high-frequency electromagnetic wave, based on a plurality of magnetic resonance images respectively corresponding to magnetic resonance signals collected during a predetermined time period.

12. The magnetic resonance diagnostic apparatus according to claim 3, wherein the heating coil periodically radiates the high-frequency electromagnetic wave, based on a plurality of magnetic resonance images respectively corresponding to magnetic resonance signals collected during a predetermined time period.

13. The magnetic resonance diagnostic apparatus according to claim 1, comprising:
   a first shield that is disposed between the gradient magnetic field coil and the high-frequency transmission coil and that serves as a shield against the high-frequency electromagnetic wave transmitted from the high-frequency transmission coil; and
   a second shield that is disposed between the first shield and the high-frequency transmission coil and that serves as a shield against the high-frequency electromagnetic wave radiated from the heating coil.

14. The magnetic resonance diagnostic apparatus according to claim 1, comprising:
   a first shield that is disposed between the gradient magnetic field coil and the high-frequency transmission coil and that serves as a shield against the high-frequency electromagnetic wave transmitted from the high-frequency transmission coil; and
   a second shield that is disposed between the first shield and the high-frequency transmission coil and that serves as a shield against the high-frequency electromagnetic wave radiated from the heating coil.

15. A magnetic resonance diagnostic apparatus comprising:
   a magnetostatic field coil that forms a magnetostatic field;
   a gradient coil that superimposes a gradient magnetic field onto the magnetostatic field;
   a high-frequency transmission coil that transmits a high-frequency electromagnetic wave at a magnetic resonance frequency to an examined subject placed in the magnetostatic field;
   a high-frequency reception coil that receives a magnetic resonance signal transmitted from the examined subject;
   an image generating unit that generates a magnetic resonance image of the examined subject, based on the magnetic resonance signal;
   a heating coil that is provided separately from the high-frequency transmission coil and that performs a heating process by radiating a high-frequency electromagnetic wave onto the examined subject at a frequency different from the magnetic resonance frequency; and
   a measuring unit that, based on the magnetic resonance signal, measures a temperature of the examined subject changing due to the high-frequency electromagnetic wave radiated by the heating coil.

16. The magnetic resonance diagnostic apparatus according to claim 15, wherein at least one pair of heating coils including the heating coil is provided, so as to have the examined subject interposed therebetween.

17. The magnetic resonance diagnostic apparatus according to claim 16, wherein one of the pair of heating coils is provided within a couchtop on which the examined subject is placed.

18. The magnetic resonance diagnostic apparatus according to claim 15, wherein the heating coil is configured in a form of a circular cylinder that surrounds the examined subject.

19. The magnetic resonance diagnostic apparatus according to claim 15, wherein the heating coil is provided inside the high-frequency transmission coil.

20. The magnetic resonance diagnostic apparatus according to claim 15, wherein the heating coil is provided at a couch including a couchtop on which the examined subject.

* * * * *